United States Patent
Wada et al.

(10) Patent No.: US 7,110,901 B2
(45) Date of Patent: *Sep. 19, 2006

(54) CORRECTION METHOD FOR SENSOR OUTPUT

(75) Inventors: Atsusi Wada, Kyoto (JP); Kouji Egawa, Kyoto (JP)

(73) Assignee: Arkray, Inc., Kyoto (JP)

( * ) Notice: Subject to any disclaimer, the term of this patent is extended or adjusted under 35 U.S.C. 154(b) by 413 days.

This patent is subject to a terminal disclaimer.

(21) Appl. No.: 10/415,991

(22) PCT Filed: Nov. 9, 2001

(86) PCT No.: PCT/JP01/09850

§ 371 (c)(1),
(2), (4) Date: May 6, 2003

(87) PCT Pub. No.: WO02/39076
PCT Pub. Date: May 16, 2002

(65) Prior Publication Data

US 2004/0034494 A1 Feb. 19, 2004

(30) Foreign Application Priority Data

Nov. 10, 2000 (JP) .............................. 2000-343365

(51) Int. Cl.
*G01D 18/00* (2006.01)
*G11B 7/00* (2006.01)

(52) U.S. Cl. ........................................ 702/86; 369/100

(58) Field of Classification Search ............... 702/86; 369/100; 382/318, 154
See application file for complete search history.

(56) References Cited

U.S. PATENT DOCUMENTS

2004/0076325 A1* 4/2004 Wada et al. ................ 382/154

FOREIGN PATENT DOCUMENTS

| JP | 03-204285 A1 | 9/1991 |
| JP | 03-289777 A1 | 12/1991 |
| JP | 03289777 A * | 12/1991 |

(Continued)

OTHER PUBLICATIONS

Na et al., Velocity-Controlled Shape-Tracing System Using Eight Optical Sensors, Sep. 1988, IEEE Transactions on Instrumentation and Measurement, vol. 37, No. 3, pp. 458-461.*

(Continued)

*Primary Examiner*—John Barlow
*Assistant Examiner*—Toan M. Le
(74) *Attorney, Agent, or Firm*—Rader, Fishman & Grauer

(57) ABSTRACT

Above a measuring object (2), an LEDs (4) for use in light irradiation and a CMOS area sensor (8) with an image-forming lens (6) interpolated in between are installed. In order to detect the quantity of light from the LEDs (4), a photodetector (10) is further placed. A personal computer (28) carries out a linearizing process which, upon variation of the quantity of light, corrects the output of the area sensor (8) so as to make the output from the area sensor (8) proportional to the output of the photodetector (10), and a light-irregularity correction process which, when a flat plate having even in-plane density is measured as the measuring object (2), corrects the resulting output of each pixel in the area sensor (8) that has been corrected by the linearizing process to have in-plane evenness. It becomes possible to achieve a convenient two-dimensional reflection factor measuring method which does not need any mechanical driving system.

9 Claims, 26 Drawing Sheets

FOREIGN PATENT DOCUMENTS

| | | | |
|---|---|---|---|
| JP | 05-297142 | A1 | 11/1993 |
| JP | 06-225143 | A1 | 8/1994 |
| JP | 08-128922 | A1 | 5/1996 |
| JP | 11-249004 | A1 | 9/1999 |
| JP | 11-329340 | A1 | 11/1999 |
| JP | 2000-013807 | A1 | 1/2000 |
| JP | 2002-512492 | A1 | 4/2002 |
| WO | 99/55081 | A1 | 10/1999 |
| WO | 01/35063 | A1 | 5/2001 |

OTHER PUBLICATIONS

Chang et al., Log-Converting Processor Element for CCD Linear Imaging Arrays, Nov. 15, 1983, Applied Optics, vol. 22, No. 22, pp. 3569-3571.*

International Search Report for PCT/JP01/09850 mailed on Jan. 22, 2002.

International Preliminayr Examination Report completed on Aug. 28, 2002.

* cited by examiner

LIGHT QUANTITY (VOLTAGE VALUE mV) -OUTPUT OF AREA SENSOR

LIGHT QUANTITY (VOLTAGE VALUE mV)
-AREA SENSOR A/D OUTPUT LINEARIZING CORRECTED

REFLECTION FACTOR-AREA SENSOR
A/D VALUE OUTPUT FOR ONE PIXEL

CORRECTION METHOD FOR SENSOR OUTPUT

FIELD OF THE INVENTION

The present invention relates to a method in which light is applied to a measuring object and measurements are carried out by receiving light reflected from a detection subject portion by a sensor, and, more specifically, concerns a correction method for a sensor output when the sensor used in this method does not have output linearity with respect to the quantity of received light.

In the present invention, the light to be measured includes various kinds of light, such as reflected light, transmitted light, fluorescent light, phosphor light and chemically emitted light, which are used in quantitative measurements and qualitative measurements.

BACKGROUND OF THE INVENTION

Photodetectors include a photodetector element constituted by a single element such as a photodiode, a linear sensor constituted by photodetector elements that are aligned on a line, such as a photodiode array, and an area sensor constituted by photodetector elements that are arranged two-dimensionally, such as a CCD sensor and a CMOS sensor.

With respect to sensor output characteristics relating to quantity of received light, there are not only sensors having linearity such as photodiodes, but also sensors having sensing characteristics that have deviations in linearity depending on areas having a small quantity of received light and those having a great quantity of received light, as in the case of area sensors such as CCD sensors and MOS sensors. Those sensors that lack linearity have been considered to be unsuitable for quantitative measurements.

Therefore, the objective of the present invention is to solve problems with linearity that occur when a sensor that lacks linearity in its output characteristics is used in a detector, and consequently to make such a sensor applicable to corresponding measurements.

DISCLOSURE OF THE INVENTION

The present invention relates to a method which applies light to a measuring object and carries out measurements by receiving light reflected from a detection subject portion by a sensor, and in such a method, with respect to the sensor, such a sensor that lacks linearity in its output in response to the quantity of received light is used Further, the present invention is characterized by a linearizing process that corrects the sensor output so that the output from the sensor in response to a variation in the quantity of received light in the sensor is made proportional to the quantity of received light.

In accordance with a first aspect, the linearizing process includes the following processes (A) and (B):
(A) A process in which a photodetector having linearity in its output in response to the quantity of received light is arranged so that light to be made incident on the sensor is simultaneously made incident on the photodetector, and upon variation in the quantity of incident light, the relationship between the sensor output and the output of the photodetector is stored as linearizing data; and
(B) A process in which, upon measurement of a measuring object, the resulting sensor output is corrected and made proportional to the output of the photodetector based upon the linearizing data.

Although the sensor output does not have linearity with respect to the quantity of received light, it is corrected so as to be made proportional to the output of the photodetector whose output has linearity with respect to the quantity of received light based upon the linearizing data; thus, the corrected sensor output is allowed to have linearity with respect to the quantity of received light.

In accordance with a second aspect, the linearizing process includes the following processes (A) and (B):
(A) A process in which a plurality of standard plates which generate mutually different light rays that have been known are prepared, and after measuring each of these standard plates, the relationship between the sensor output and light from each of the standard plates is stored as linearizing data.
(B) A process in which the sensor output obtained upon measuring a measuring object is corrected so as to be made proportional to light from the standard plate based upon the linearizing data.

In this case also, although the sensor output does not have linearity with respect to the quantity of received light, it is corrected so as to be made proportional to light from the standard plate based upon the linearizing data; thus, the corrected sensor output is allowed to have linearity with respect to the quantity of received light In the second aspect, it is not necessary to separately install a light-quantity-monitoring photodetector whose output has linearity with respect to the quantity of received light and a measuring device for the photodetector. In this method, after adjusting the light quantity of a light source, the standard plate is exchanged and a measurement is simply carried out so that the operation is easily carried out Moreover, since the correction is made by using data derived from light actually received by the sensor, it is possible to reduce error factors.

In accordance with a third aspect, the linearizing process includes the following processes (A) and (B):
(A) A process in which a sensor is allowed to variably set exposing time, and upon measuring one reference object the relationship between each of sensor outputs obtained from measurements carried out while changing the exposing time in a plurality of stages and the corresponding exposing time is stored as linearizing data relating to light from the reference object, which is proportional to the exposing time, and
(B) A process in which the sensor output, obtained upon measuring a measuring object, is corrected so as to be made proportional to light from the reference object that is found by the exposing time based upon the linearizing data.

With respect to the reference object, for example, a reflection plate having even in-plane density or a blank state (a state in which all the measuring light is made incident on an image sensor without placing a measuring object) is prepared.

In the third aspect, the quantity of received light of the sensor is proportional to exposing time during which the reference object is exposed. In this case also, although the sensor output does not have linearity with respect to the quantity of received light, it is corrected so as to be made proportional to light from the reference object which is found from the exposing time, based upon the linearizing data; thus, the corrected sensor output is allowed to have linearity with respect to the quantity of received light.

In accordance with the third aspect, in addition to the advantages obtained by the second aspect, without the necessity of a plurality of standard plates, linearizing data can be formed by using only one sheet of reference object that forms the standard; therefore, it is possible to make the operation easier.

In this aspect, by installing, for example, a reference white plate in the device as the reference object, it becomes possible to easily obtain linearizing data in each of the measurements or in appropriate intervals. Moreover, it is possible to easily obtain linearizing data automatically, and consequently to desirably maintain measuring precision.

An example of a sensor suitable for use in accordance with the present invention is an area sensor. In this case, the above-mentioned linearizing process is carried out on each pixel. Moreover, the linearizing process may be carried out by selecting some of pixels in the vicinity of pixels that are brightest within an image and using the average value of the outputs of these pixels.

Examples of the area sensor include those of the CCD type or CMOS type.

The output of the sensor is preferably prepared as a value that has been subjected to an offset process, that is, a value obtained by subtracting an output at the time when the quantity of received light is zero as dark data.

An example of an analyzer to which the sensor is applied is a reflectance measuring device. With respect to the sensor in the reflectance measuring device, a photodiode has been mainly used from the viewpoint of superior precision, cost performance and technical easiness. However, in an attempt to obtain reflectances of a plurality of items by using the photodiode, an optical system or a test sample needs to be shifted. Moreover, since the photodiode is used for obtaining data that is averaged within a spot diameter, it is not suitable for use in precisely detecting color developments, as typically exemplified by detection of spot color developments.

In order to solve these problems, the application of an area sensor is proposed. Since data of the area sensor is image information relating to a target area, measurements of a plurality of items, detection of spot color developments, correction of positional deviations in test samples, etc. may be carried out based upon information of one frame.

Detections of the shape and color of a subject by the use of an area sensor have been well-known. For example, a method in which an image of a test strip for use in immunization measurements is picked up by a CCD camera so that determination is made based upon the area or the ratio of the longitudinal and lateral lengths of the image has been proposed (see Japanese Patent Application Laid-Open No. 9-257708). In this method, after the picked-up signal has been binarized as a luminance signal, the shape of an image is measured; therefore, this method is not used for measuring the density within the image.

With respect to another example in which two-dimensional measurements are carried out by using an area sensor, a urine measuring device is listed. In this device, in general, measurements are carried out by determining not the density (brightness) in color developments, but the color gradation (hue) in urine test paper, and a color-CCD device is used.

In an attempt to detect a two-dimensional density distribution of a measuring object with high precision by using an area sensor, in addition to irradiation irregularities in light, lens aberration, etc., in-plane light irregularities occur due to a sensitivity difference between pixels of the area sensor. For this reason, in order to carry out detections with high precision, in general, the sensor or the measuring object is shifted by using a mechanical driving system. In such a case, even if the area sensor is applied, it is merely utilized as a one-dimensional linear sensor.

In an attempt to carry out quantitative measurements based upon light from a measuring object by using an area sensor, in addition to the above-mentioned problems with non-linearity, the following problems are raised. In other words, since an attempt to carry out two-dimensional measurements causes in-plane light irregularities due to irradiation irregularities in light, lens aberration, deviations in pixel sensitivity depending on places, and the like; consequently, the two-dimensional measurements result in positional deviations in the results of the quantitative measurements.

Therefore, in order to achieve a convenient two-dimensional measuring method by using an area sensor without the necessity of a mechanical driving system, it is preferable to further provide a light-irregularity correction process which, after a reference object has been measured as a measuring object, corrects the outputs of the respective pixels so that corrected values, obtained by subjecting the corresponding outputs of the respective pixels of the area sensor to the above-mentioned linearizing process, are evenly adjusted.

The raw image information, picked up by the measuring device using the area sensor, is subjected to influences from individual differences in sensitivity of the respective pixels, irradiation irregularities of a light source (for example, LED), cosine quadruple rule (aberration) of the lens and the like. The "light irregularities" are caused by all these influences.

Since the output from the area sensor is allowed to have linearity by the linearizing process, the light irregularity correction process makes it possible to further eliminate the in-plane light irregularities so that it becomes possible to carry out two-dimensional measurements with high precision without the necessity of using a mechanical driving system.

One of the methods for the light irregularity correction process is a method in which a reference object is measured as a measuring object, and the correction process is carried out on image data by using a fixed rate of the quantity of received light with respect to the quantity of light at the time when the quantity of received light of the pixels has reached the quantity of the saturated light The corresponding rate is set to a value, for example, 0.8, which is comparatively close to the saturated quantity of light; thus, it becomes possible to carry out the light irregularity correction process with high precision.

With respect to the area sensor, a sensor of the CCD (charge coupled device) type or the CMOS type may be used.

By carrying out the linearizing process using the present invention, it is possible to carry out quantitative measurements even in the case when a sensor whose output does not have linearity with respect to the quantity of received light is used.

By further carrying out the light irregularity correction process, the following effects can be achieved through measurements by the use of the area sensor.

(1) Upon carrying out measurements on urine test paper or the like, it is also possible to measure items which have the same hue with varied densities.

(2) In comparison with a device that needs a mechanical driving system, the speed in which the entire image is picked up is faster, making it possible to provide high-speed measuring processes.

(3) It is possible to achieve low costs since no mechanical driving system is required.

BRIEF DESCRIPTION OF THE DRAWINGS

FIG. 2 shows specific examples of optical systems in the reflection-factor measuring device of FIG. 1.

FIG. 7 is a drawing that shows one example of correcting processes.

FIG. 8 shows three-dimensional contour face graphs obtained by picking up images of a white plate in a separate manner into three stages from dark to bright in the quantity of LEDs light and aligning the pieces of image information.

FIG. 6 is a plan view that shows pixel positions that are subjected to light-irregularity corrections.

BEST MODE FOR CARRYING OUT THE INVENTION

The following description will exemplify a case in which a reflection factor is measured; however, not limited to the reflection factor, the present invention may also be applied to measurements of transmittance, fluorescent light, phosphor light, chemically emitted light and the like, in the same manner.

Embodiment 1

Figure 1:
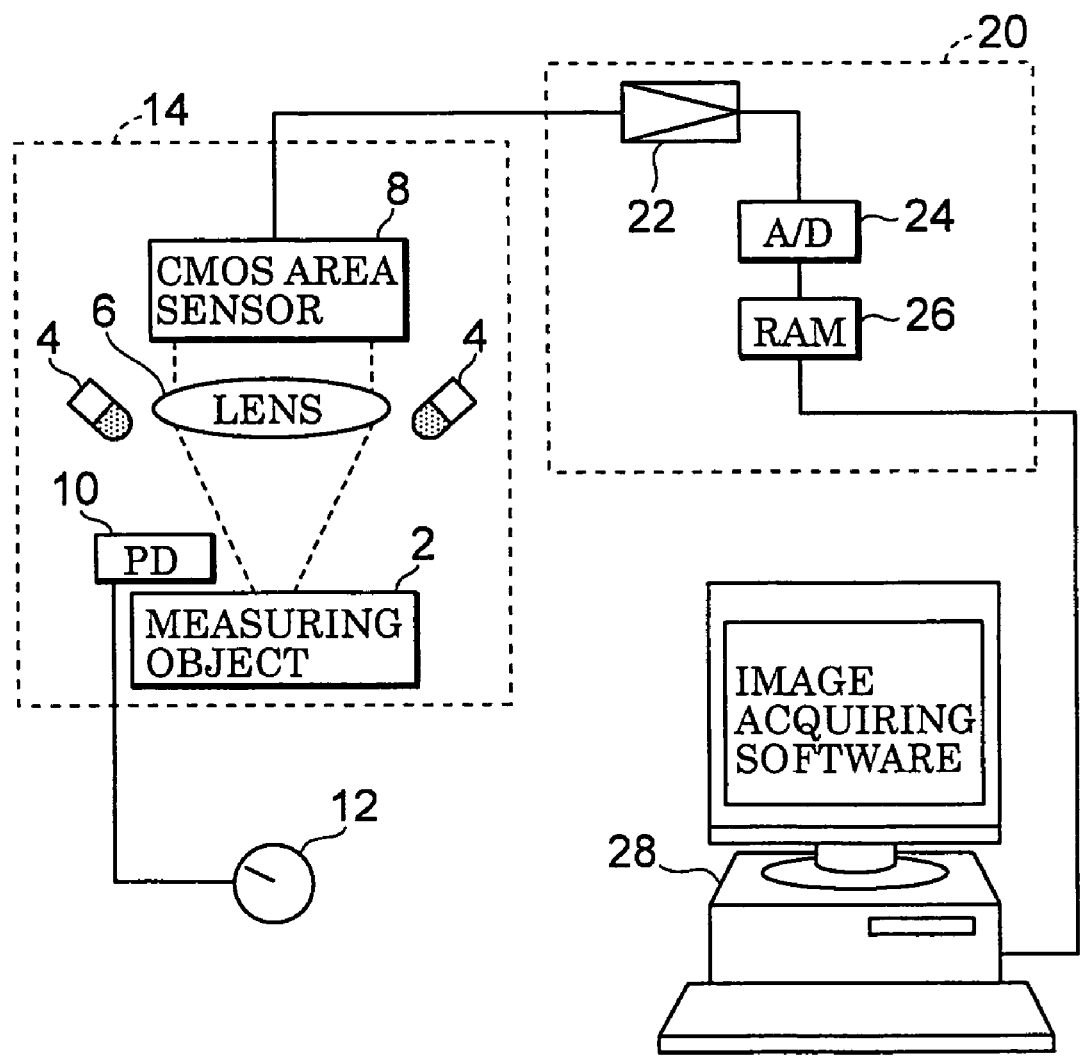
FIG. 1 is a partial block diagram that shows one example of a reflection-factor measuring device to which the present invention is applied.

With respect to a first embodiment, FIG. 1 schematically shows one example of a two-dimensional reflection-factor measuring device to which an output correction method in accordance with the first aspect of the present invention is applied with an area sensor being used as the sensor.

Reference numeral 2 is a measuring object which is held on a sample base (not shown in Figures), and placed at a predetermined position. Upon actual measurements such as a clinical inspection, the measuring object 2 is test paper such as urine test paper and immunization measuring use test paper, and a thin-layer chromatograph in a chemical analysis; however, in the case when an area sensor is corrected, a white plate having even reflection factor on the surface corresponds to the measuring object In order to irradiate the measuring object 2, three LEDs (light-emitting diodes) 4 serving as light sources are placed above the periphery of the measuring object 2 at the same level with 120-degree intervals from each other so as to apply light beams to the center of the measuring object 2 with an incident angle of 45 degrees. Each of the LEDs 4 has a center wavelength of 635 nm in its light emission.

A CMOS area sensor 8 is placed above the measuring object 2 through an image-converging lens 6. A reflected light from the measuring object 2 is converged to form an image on the area sensor 8 by the lens 6 so that image information of the measuring object 2 is detected by the area sensor 8.

A photodetector (PD) 10 is placed at a position out of the image angle of the area sensor 8 to sense the quantity of light from the LEDs 4. The photodetector 10 is prepared as a photodiode, and its output has linearity with respect to the quantity of received light, and converts the quantity of irradiated light applied to the measuring object 2 into a voltage. Reference numeral 12 is a voltmeter that converts the quantity of light received by the photodetector 10 into a voltage.

A broken-line block 14 represents the fact that the LEDs 4, the lens 6, the area sensor 8 and the photodetector 10 constitute an optical system of this reflection-factor measuring device.

A broken-line block 20 represents an area sensor drive circuit, and is provided with an amplifier 22 for amplifying an output of the area sensor 8, an A/D converter 24 for converting an amplified analog output to a digital signal, and a RAM (random-access-memory) 26 for temporarily holding an acquired digital signal. This area sensor drive circuit 20 controls the area sensor 8 so as to set a register for image-pickup time and to acquire image data and the like. Moreover, the area sensor drive circuit 20 adjusts the quantity of light from the LEDs 4, carries out serial communications (56000 bps) with a personal computer 28, and executes an instruction from the personal computer 28.

The personal computer 28 carries out various register settings of the area sensor 8, gives instructions to the area sensor drive circuit 20, acquires image information, and displays the image on a monitor. Moreover, it stores data in an appropriate format The personal computer 28 also achieves the above-mentioned offset processes, linearizing processes and light-irregularity correcting processes.

Figure 2A:
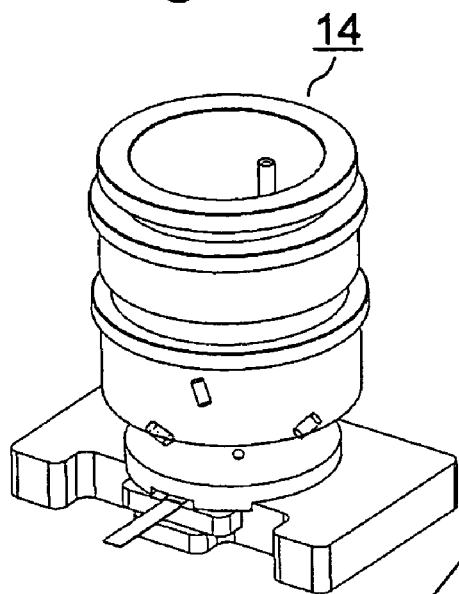
FIG. 2(a) shows an outside view of the optical system.
Figure 2B:
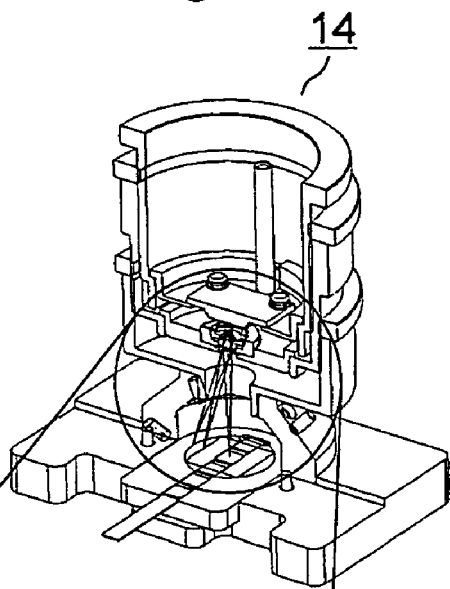
FIG. 2(b) shows a longitudinal cross-sectional view thereof.
Figure 2C:
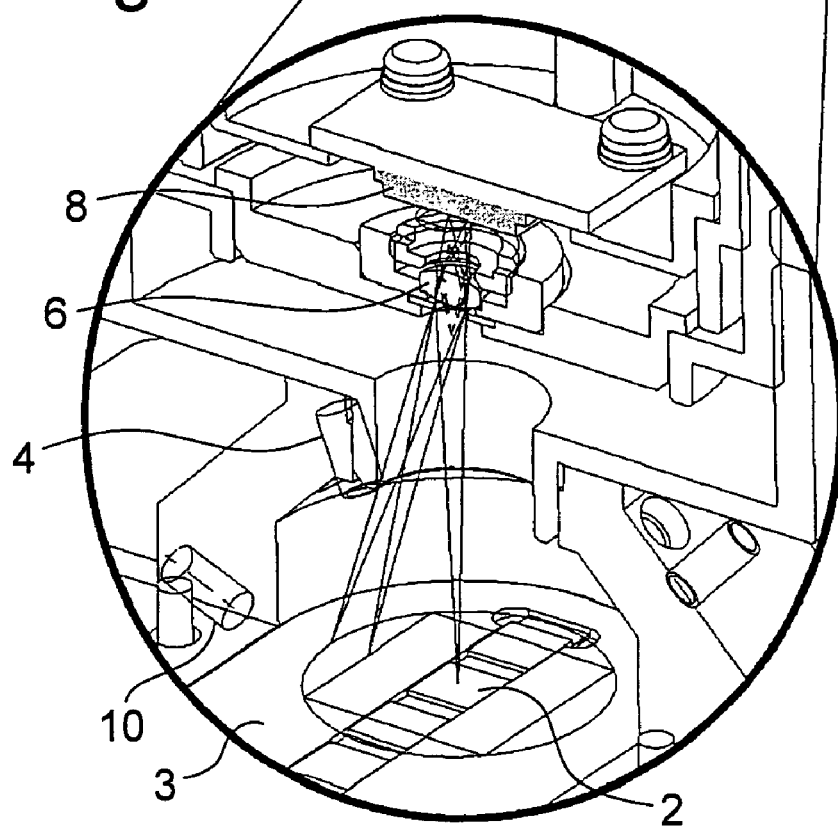
FIG. 2(c) shows an enlarged view within the circle in FIG. 2(b).

FIG. 2 shows a specific example of an optical system 14. FIG. 2(a) shows an outside view of the optical system, FIG. 2(b) shows a longitudinal cross-sectional view thereof, and FIG. 2(c) shows an enlarged view within the circle in FIG. 2(b).

This optical system has an arrangement in which the distance from the lens 6 to the measuring object 2 and the distance from the lens 6 to the area sensor 8 are finely adjusted freely; thus, it is possible to easily carry out a focusing process, a magnification-changing process and the like. Moreover, the measuring object 2 can be exchanged together with a base plate 3 of the sample base.

Reflection-factor measurements were carried out by using a CMOS image sensor (H64283FP) made by Mitsubishi Electric Corporation as the area sensor 8, and the following description will discuss the results of the measurements.

First, the following description will explain the correction process of the area sensor 8.

(1) Offset Process (Dark Process)

Supposing that the current value of the LEDs 4 is 0 (mA), the output (A/D count value) of the area sensor 8 at this time is defined as a dark (offset) state. With respect to all the calculation results (correction processes, reflection factor calculations and the like) which will be described below, a difference between the output (A/D count value) of the area sensor 8 upon irradiation by the LEDs 4 and the dark component is defined as the original output (A/D count value) of the area sensor 8.

(2) Relationship Between the Quantity of Light and the Area Sensor Output (Linearizing Correction):

The relationship between the quantity of light emitted by the LEDs 4 to the measuring object 2 and the output of the area sensor 8 (count value obtained by A/D converting Vout) is not a directly proportional relationship.

Figure 3:
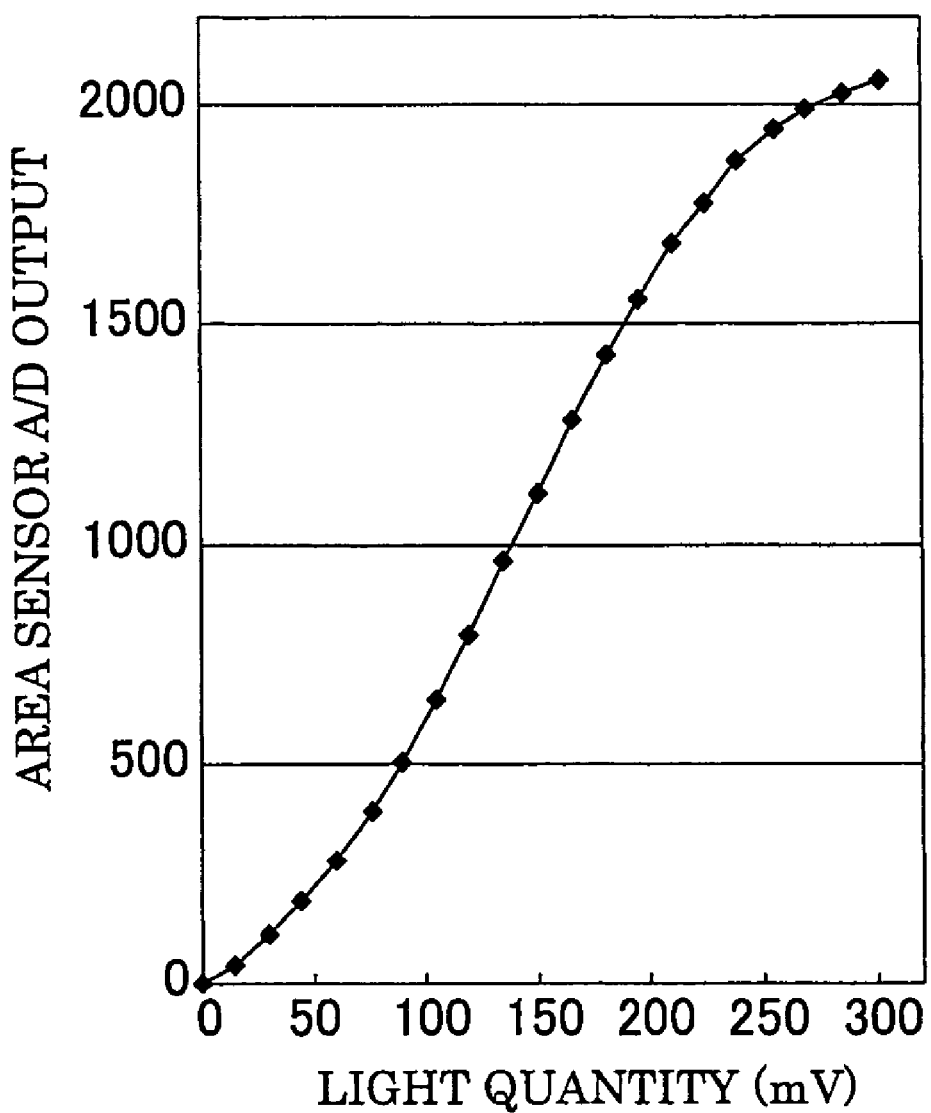
FIG. 3 is a drawing that shows the output characteristics of an area sensor.

A graph shown in FIG. 3 indicates the output of the area sensor 8 obtained by varying the quantity of light from the LEDs 4, while a white plate (ND (neutral density): 9.5, actual value of reflection factor 87.00% (the actual value of reflection factor is measured by a spectrophotometer (MINOLTA CM-503c)(the same is true for the following measurements))) is used as the measuring object 2. The axis of abscissas indicates the output (mV) of a photodetector 10 placed within the optical system 14, and the axis of ordinates indicates the average value of data of appropriate 5 pixels that are successively aligned at a portion of the area sensor 8 that receives the strongest light.

In order to correct light irregularities, it is necessary to carry out processes for converting the output (A/D count value) of the area sensor 8 to the output (mV) of the photodetector 10 as pre-processes. Prior to the light irregularity correction, characteristics shown in FIG. 3 are measured under the condition of 25° C., and based upon the results of the measurements, the output of each pixel of the area sensor 8 is corrected and calculated.

Figure 4:
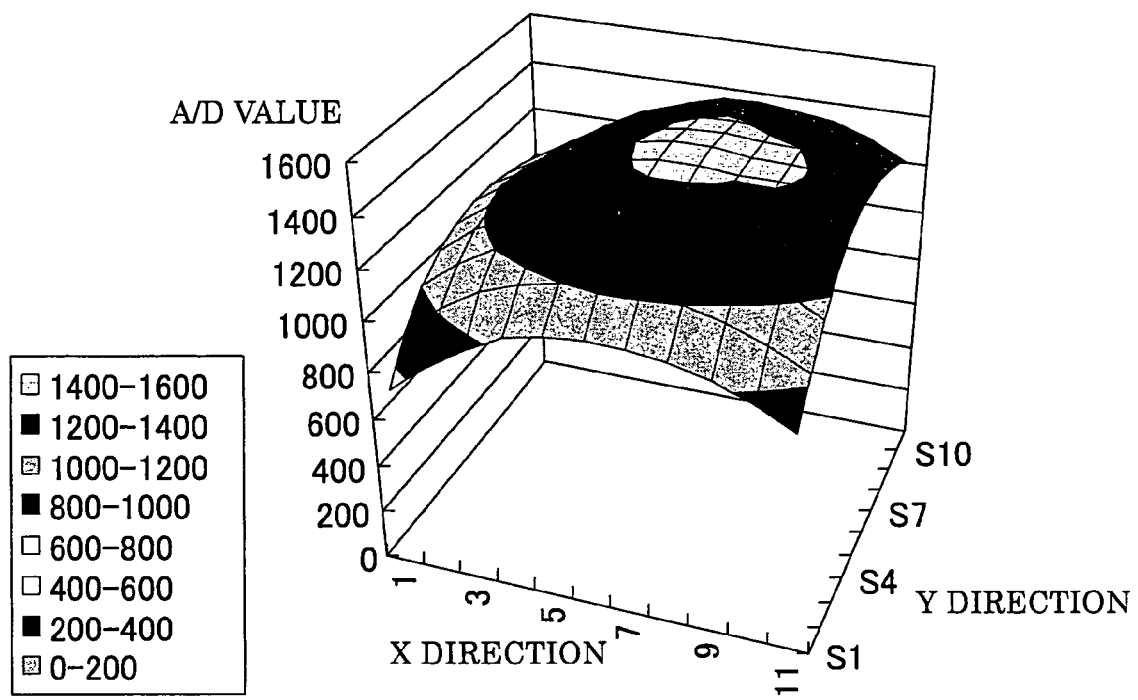
FIG. 4 is a three-dimensional contour face graph obtained when an image of a white plate is picked up by an area sensor.

(3) Image Irregularity (Light Irregularity) Correction:

The raw image information, picked up by using this reflection-factor measuring device, causes light irregularities due to influences from individual differences in sensitivity of the respective pixels in the area sensor 8, irradiation irregularities of the LEDs 4, cosine quadruple rule of the lens 6 and the like. In FIG. 4, an image of a white plate (ND: 9.5, actual value of reflection factor 87.00%)(all the image angle range is occupied by the white plate area) is picked up, and the image information is indicated by a three-dimensional contour face graph. The contour face is formed by dividing the image into 10×10 areas and using the average value of pixels contained in each of the areas.

The graph of FIG. 4 shows that, even in the case when an image of a flat face having even density, such as a white plate, is picked up, density information within the image angle is deformed into a dome shape due to influences from light irregularities. Processes for correcting such image information deformed into the dome shape to a horizontal face having even density are essential to a case in which the area sensor 8 is used as the photodetector in the reflection-factor measuring device. In the present invention, all the results of measurements are obtained by carrying out this light irregularity correction.

Figure 5:
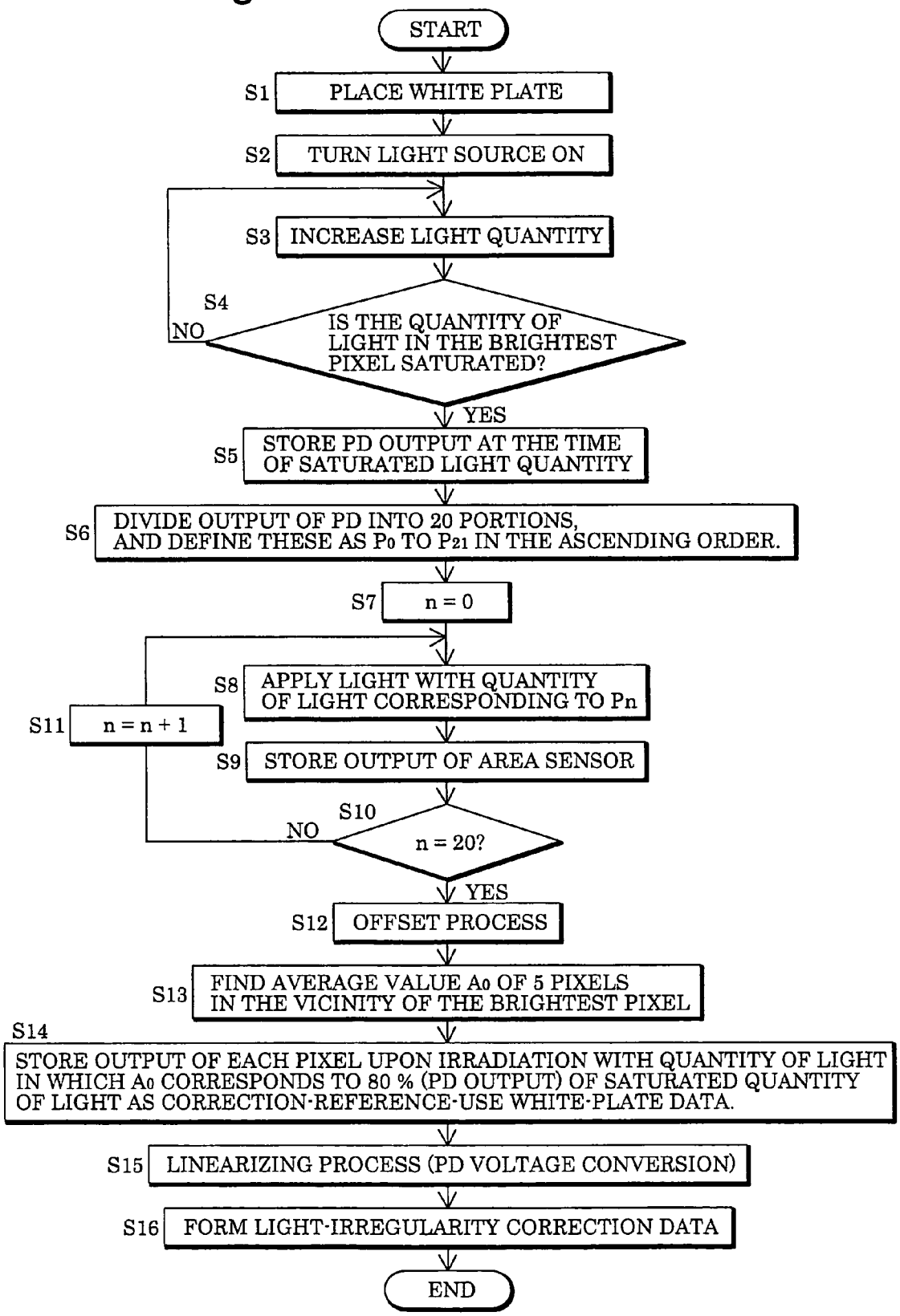
FIG. 5 is a flow chart that shows an embodiment of a correction process of the present invention.

In the present invention, the correction processes were carried out in accordance with the following sequence. Referring to FIG. 5, the sequence will be explained.

<Acquiring Sequence for Correction Reference Data>

(1) A white plate (ND: 9.5, actual value of reflection factor 87.00%) is used as the measuring object 2 so that a voltage value of the photodetector (PD) 10 is found at the time when the brightest pixel within the picked-up image has reached the saturated quantity of light (steps S1 to S5).

(2) The voltage value of the photodetector 10 obtained at the time when the pixel has reached the saturated quantity of light from 0 (mV) is divided into 20 equal portions so that respective voltage values of 21 stages are found, and these are indicated as P0 to P21 in the ascending order (step S6).

(3) The quantity of light of the LEDs 4 is adjusted so that voltage values of the photodetector 10 are set to the respective stages. Images of the white plate are picked up by using the respective quantities of light, and the pieces of corresponding data are stored (21 sheets of image data are obtained. The image corresponding to 0 (mV) is referred to as dark data.)(steps S7 to S11).

(4) All the pieces of image data are subjected to offsetting processes (that is, the value of the dark data is subtracted from each piece of image data for each pixel)(step S12).

(5) Five pixels that are successively aligned in the vicinity of the brightest pixel within the image are averaged. These processes are carried out on each image so that the relationship (see FIG. 3) between the voltage value of the photodetector 10 and the output of the area sensor is obtained (step S13).

(6) Among 21 sheets of image data, the image data corresponding to the saturated quantity of light×0.8 is selected as white-plate data for use in light-irregularity correction reference (step S14).

<Light-irregularity Correction Sequence of Measured Image>

(7) A/D data corresponding to each of 128×128 pixels of a measured image is converted to a voltage value of the photodetector 10 based upon the relationship shown in FIG.

3 (PD voltage-value conversion: linearizing process)(step S15). The conversion is carried out by linearly interpolating gaps between sample points in the graph of FIG. 3.

(8) With respect to the light-irregularity correction-reference-use white plate data obtained in the process (6), the PD voltage value conversion is carried out in the same manner.

(9) The ratio of the measured image data (after the PD voltage-value conversion) to the light-irregularity correction-reference-use white plate data (after the PD voltage-value conversion) is found for each of 128×128 pixels. This ratio is set as light-irregularity correction data (step S16).

(Example of Pixel Correction)

The following description will explain an example in which the quantity of reflected light is found from the resulting output from each of the pixels by using the above-mentioned correction method. Pixels to be corrected are five points shown in FIG. 6, which are respectively set to point 1 (32, 32), point 2 (96, 32), point 3 (64, 64), point 4 (32, 96) and point 5 (96, 96).

Figure 6:
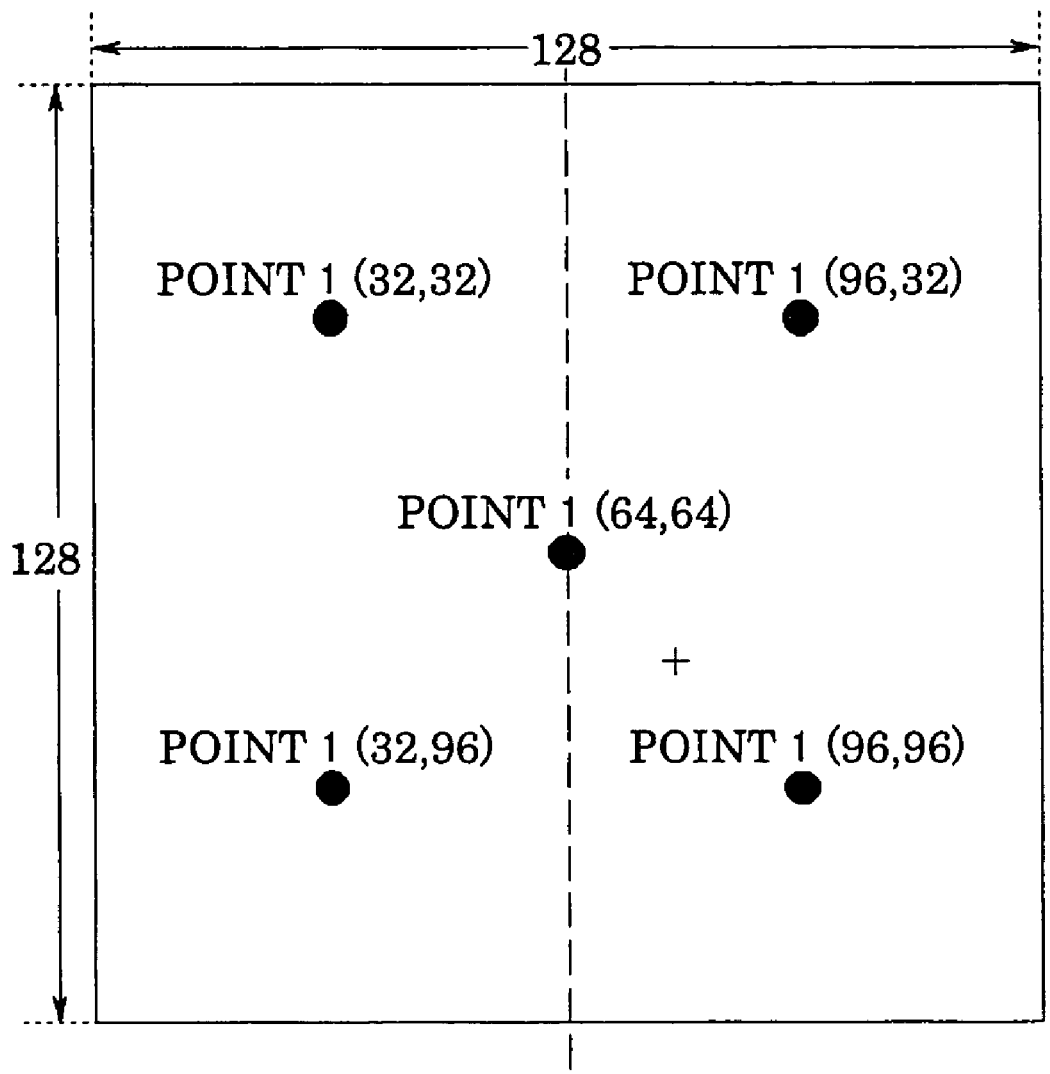
FIG. 6 is a plan view that shows a position of a pixel from which data is acquired.
Figure 7A:
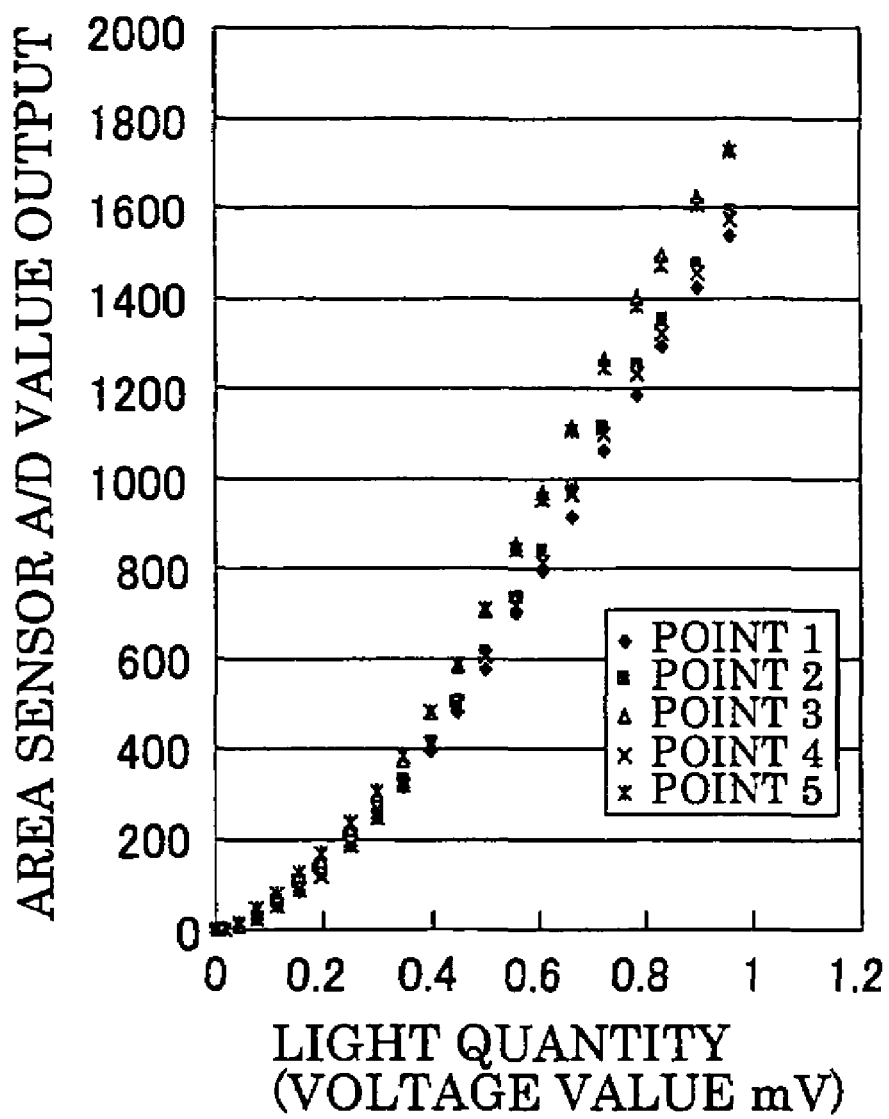
FIG. 7(a) is a graph that shows respective pixel outputs of an area sensor when a white plate is used as a measuring object.

FIG. 7(a) shows a graph that indicates outputs at five points of the area sensor shown in FIG. 6 at the time when the quantity of light of the LEDs 4 is varied with a white plate (ND: 9.5, actual value of reflection factor. 87.00%) being used as the measuring object 2.

Figure 7B:
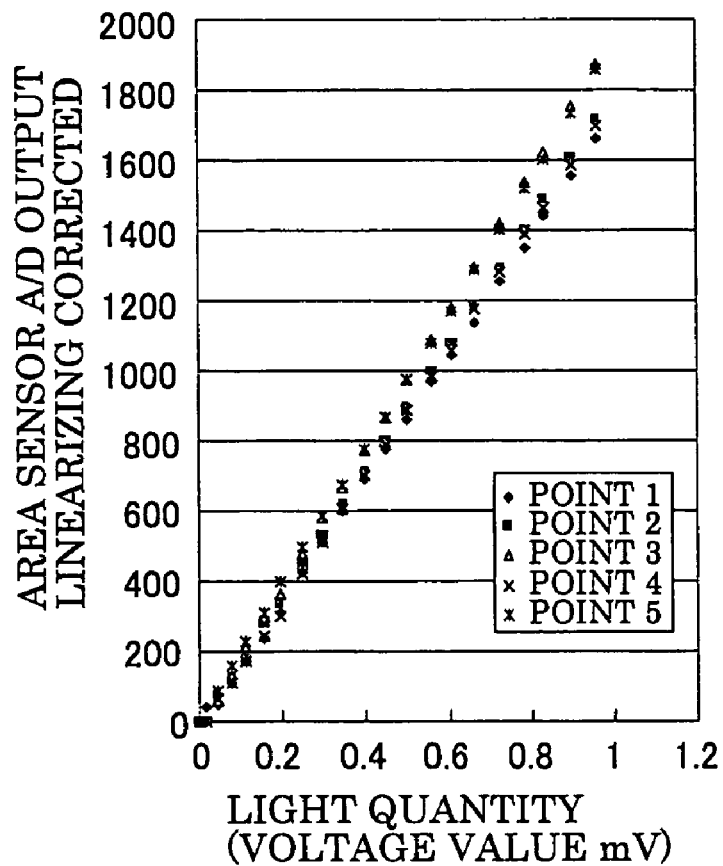
FIG. 7(b) is a graph that shows an output after a PD voltage-value conversion.

When the area sensor output (A/D count value) is converted (PD voltage-value conversion) to a voltage value of the photodetector based upon the relationship indicated by the graph of FIG. 3, the resulting correction as shown in FIG. 7(b) is obtained. In FIG. 7(b), there are differences among the quantities of reflected light at the respective points due to influences resulting from light irregularities and the like; however, the respective points are allowed to have a direct proportional relationship with respect to the quantity of light of the LEDs 4.

Figure 7C:
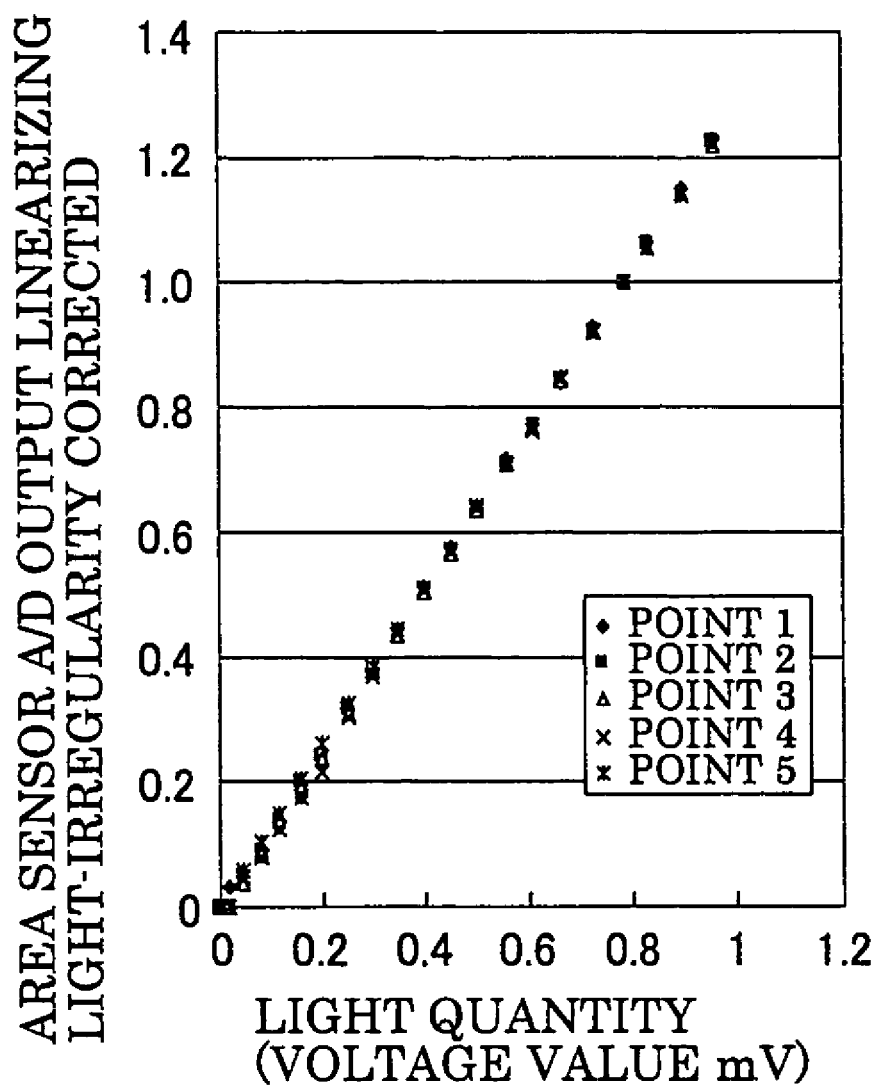
FIG. 7(c) is a graph obtained when the output of FIG. 7(b) is further subjected to a light irregularity correction process.

FIG. 7(c) shows a graph in which the light irregularities are corrected by applying the light-irregularity correction data to FIG. 7(b). The respective points are plotted along virtually the same line. The reason that, in FIG. 7(c), five points are completely made coincident with each other when the correction output of the area sensor is 1 is because light irregularities have been corrected based on the white plate data at this brightness. FIG. 7(c) also shows that as the quantity of light decreases, the respective points come to deviate, resulting in degradation in correction precision.

(Example of Area Correction)

Figure 8A:
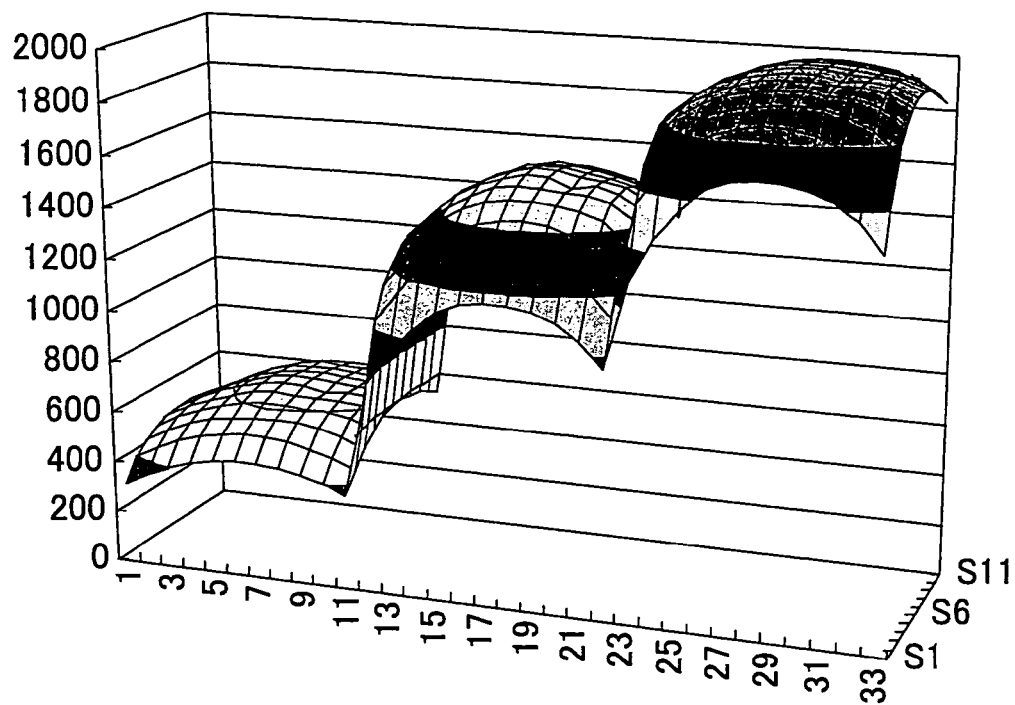
FIG. 8(a) shows a state prior to the light-irregularity correction.

FIG. 8(a) shows a graph that is obtained by picking up images of the white plate (ND: 9.5, actual value of reflection factor 87.00%) in a manner so as to be divided three stages from dark to bright in the quantity of LEDs light (all the image angle range is occupied by the white plate area), and aligning the pieces of image information to form a three-dimensional contour face graph. The contour face is formed by dividing the image into 10×10 areas and using the average value of pixels contained in each of the areas. With respect to the three dome-shaped white plate data, the data on the left end relates to the smallest quantity of light and the data on the right end relates to the greatest quantity of light.

The white plate data on the right end has a narrow difference between the maximum value and the minimum value even though the quantity of light thereof is greater than that of the white plate data in the middle. This is because the pixel quantity of light at a brighter portion of the white plate is close to the saturated quantity.

Figure 8B:
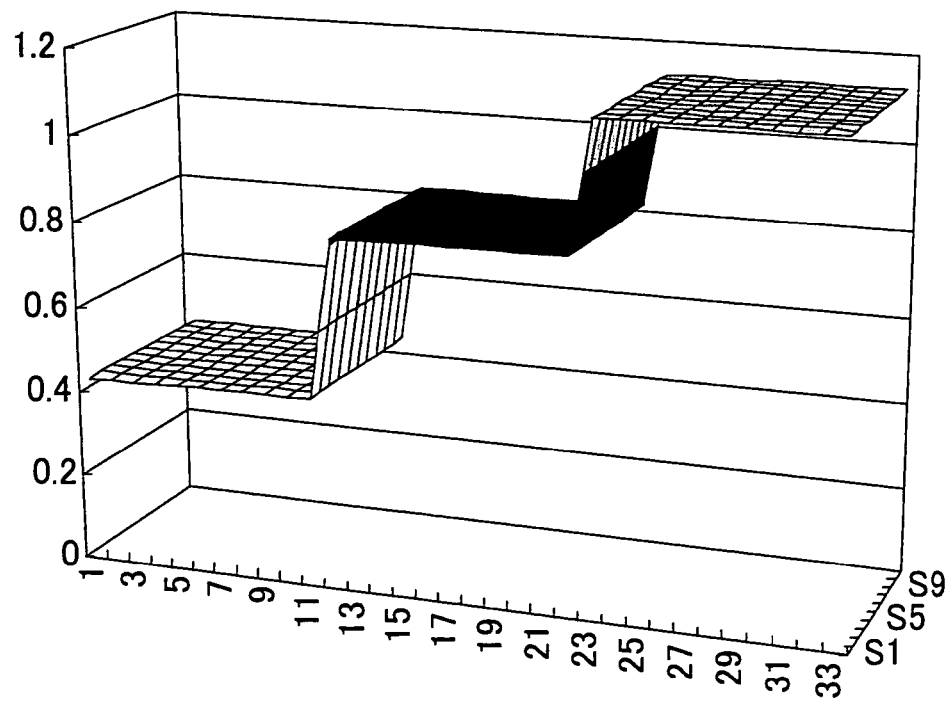
FIG. 8(b) shows a state in which the graph of FIG. 8(a) has been subjected to light-irregularity correction processes.

When the light-irregularity correction is carried out on the graph of FIG. 8(a), a flat graph is obtained as shown in FIG. 8(b).

(Simultaneous Reproducibility 1)

With respect to the same pixel, images of pieces of ND paper having different reflection factors were picked up, and the simultaneous reproducibility, obtained in the case when the ratio of the density values of these is calculated as a reflection factor, was examined.

The following description will discuss the sequence of the processes.

(1) The current value of the LEDs 4 is set to 0 mA, and a dark (offset) image is picked up.

(2) Plates formed by bonding pieces of paper of ND 9.5 (actual value of reflection factor 87.00%) and ND 6.5 (actual value of reflection factor 36.21%) onto base plates are prepared, and images of these are alternately picked up ten times.

Figure 9:
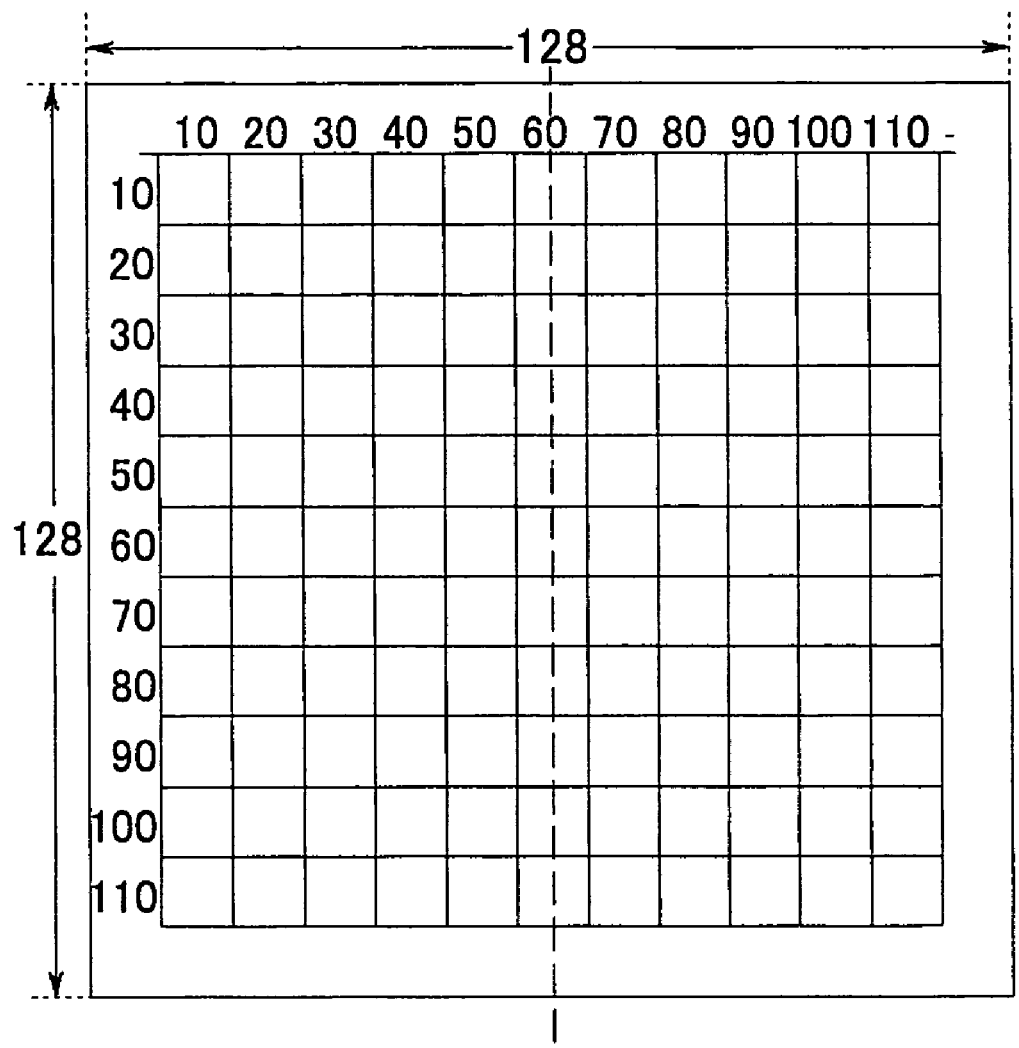
FIG. 9 is a plan view that shows an example in which one sheet of an image is divided into 11×11 areas.

(3) After light irregularities of the respective pixels have been corrected, one sheet of image is divided into 11×11 areas (each area containing 10×10=100 pixels) as shown in FIG. 9, and the average value of the quantities of light of the respective areas is calculated. The ratio of ND 9.5 and ND 6.5 of this average value of quantities of light is used as a reflection factor so that calculations are carried out on the respective areas.

Table 1 shows the results of measurements of one time among the measurements carried out ten times. The upper stage of this Table shows the average of light quantities of the respective areas obtained when an image of ND 9.5 is picked up, the intermediate stage thereof shows the average of light quantities of the respective areas obtained when an image of ND6.5 is picked up, and the lower stage thereof shows the rate of respectively identical areas that is found as the reflection factor.

TABLE 1

No.1

| | LIGHT QUANTITY BLOCK AVERAGE DISTRIBUTION (ND: 9.5, ACTUAL VALUE: 87.00%) | | | | | | | | | | | |
|---|---|---|---|---|---|---|---|---|---|---|---|---|
| | 0 | 10 | 20 | 30 | 40 | 50 | 60 | 70 | 80 | 90 | 100 | 110 |
| 0 | | | | | | | | | | | | |
| 10 | | 1.023 | 1.023 | 1.024 | 1.022 | 1.022 | 1.022 | 1.022 | 1.022 | 1.022 | 1.022 | 1.022 |
| 20 | | 1.024 | 1.023 | 1.023 | 1.023 | 1.023 | 1.023 | 1.023 | 1.023 | 1.023 | 1.022 | 1.021 |
| 30 | | 1.023 | 1.023 | 1.023 | 1.023 | 1.024 | 1.023 | 1.023 | 1.023 | 1.023 | 1.023 | 1.023 |
| 40 | | 1.022 | 1.024 | 1.023 | 1.023 | 1.023 | 1.023 | 1.023 | 1.023 | 1.023 | 1.023 | 1.023 |
| 50 | | 1.023 | 1.024 | 1.023 | 1.024 | 1.023 | 1.022 | 1.023 | 1.023 | 1.022 | 1.024 | 1.023 |
| 60 | | 1.023 | 1.023 | 1.023 | 1.023 | 1.022 | 1.022 | 1.023 | 1.023 | 1.023 | 1.023 | 1.022 |
| 70 | | 1.023 | 1.023 | 1.023 | 1.023 | 1.023 | 1.023 | 1.022 | 1.022 | 1.023 | 1.022 | 1.022 |

TABLE 1-continued

No.1

| | | | | | | | | | | | |
|---|---|---|---|---|---|---|---|---|---|---|---|
| 80 | 1.023 | 1.024 | 1.024 | 1.024 | 1.023 | 1.022 | 1.023 | 1.023 | 1.022 | 1.022 | 1.022 |
| 90 | 1.023 | 1.024 | 1.024 | 1.023 | 1.023 | 1.022 | 1.023 | 1.023 | 1.023 | 1.022 | 1.023 |
| 100 | 1.023 | 1.024 | 1.024 | 1.023 | 1.023 | 1.023 | 1.023 | 1.022 | 1.023 | 1.023 | 1.022 |
| 110 | 1.025 | 1.023 | 1.023 | 1.024 | 1.023 | 1.023 | 1.023 | 1.023 | 1.023 | 1.023 | 1.022 |
| 120 | | | | | | | | | | | |
| AVE. | 1.023 | | | | | | | | | | |
| C.V.(%) | 0.060 | | | | | | | | | | |
| ⊿ | 0.003 | | | | | | | | | | |

LIGHT QUANTITY BLOCK AVERAGE DISTRIBUTION
(ND: 6.5, ACTUAL VALUE: 36.21%)

| | 0 | 10 | 20 | 30 | 40 | 50 | 60 | 70 | 80 | 90 | 100 | 110 |
|---|---|---|---|---|---|---|---|---|---|---|---|---|
| 0 | | | | | | | | | | | | |
| 10 | | 0.419 | 0.419 | 0.423 | 0.421 | 0.420 | 0.421 | 0.422 | 0.426 | 0.431 | 0.438 | 0.450 |
| 20 | | 0.421 | 0.420 | 0.422 | 0.423 | 0.422 | 0.422 | 0.423 | 0.426 | 0.431 | 0.439 | 0.445 |
| 30 | | 0.419 | 0.421 | 0.422 | 0.424 | 0.423 | 0.422 | 0.422 | 0.425 | 0.429 | 0.437 | 0.444 |
| 40 | | 0.419 | 0.423 | 0.423 | 0.421 | 0.420 | 0.421 | 0.422 | 0.424 | 0.426 | 0.433 | 0.442 |
| 50 | | 0.419 | 0.421 | 0.422 | 0.421 | 0.419 | 0.420 | 0.420 | 0.422 | 0.425 | 0.432 | 0.439 |
| 60 | | 0.418 | 0.421 | 0.421 | 0.420 | 0.419 | 0.419 | 0.420 | 0.422 | 0.424 | 0.430 | 0.437 |
| 70 | | 0.418 | 0.420 | 0.421 | 0.420 | 0.419 | 0.417 | 0.419 | 0.422 | 0.426 | 0.429 | 0.436 |
| 80 | | 0.418 | 0.422 | 0.422 | 0.420 | 0.419 | 0.419 | 0.417 | 0.421 | 0.424 | 0.427 | 0.435 |
| 90 | | 0.418 | 0.422 | 0.423 | 0.422 | 0.418 | 0.419 | 0.418 | 0.420 | 0.424 | 0.430 | 0.437 |
| 100 | | 0.418 | 0.419 | 0.423 | 0.423 | 0.420 | 0.417 | 0.418 | 0.419 | 0.426 | 0.431 | 0.438 |
| 110 | | 0.418 | 0.419 | 0.421 | 0.422 | 0.420 | 0.420 | 0.421 | 0.421 | 0.425 | 0.434 | 0.442 |
| 120 | | | | | | | | | | | | |
| AVE. | 0.424 | | | | | | | | | | | |
| C.V.(%) | 1.610 | | | | | | | | | | | |
| ⊿ | 0.032 | | | | | | | | | | | |

IDENTICAL AREA REFLECTION FACTOR

| | 0 | 10 | 20 | 30 | 40 | 50 | 60 | 70 | 80 | 90 | 100 | 110 |
|---|---|---|---|---|---|---|---|---|---|---|---|---|
| 0 | | | | | | | | | | | | |
| 10 | | 40.92 | 40.91 | 41.34 | 41.13 | 41.11 | 41.14 | 41.29 | 41.73 | 42.12 | 42.86 | 43.99 |
| 20 | | 41.06 | 41.04 | 41.29 | 41.33 | 41.22 | 41.22 | 41.40 | 41.63 | 42.16 | 42.93 | 43.56 |
| 30 | | 40.98 | 41.18 | 41.25 | 41.41 | 41.32 | 41.28 | 41.28 | 41.54 | 41.95 | 42.72 | 43.44 |
| 40 | | 41.01 | 41.26 | 41.31 | 41.19 | 41.04 | 41.12 | 41.26 | 41.45 | 41.70 | 42.36 | 43.21 |
| 50 | | 40.96 | 41.15 | 41.25 | 41.14 | 40.94 | 41.04 | 41.03 | 41.28 | 41.54 | 42.17 | 42.92 |
| 60 | | 40.87 | 41.18 | 41.14 | 41.03 | 41.00 | 40.99 | 41.07 | 41.25 | 41.48 | 42.07 | 42.73 |
| 70 | | 40.83 | 41.04 | 41.14 | 41.08 | 41.00 | 40.82 | 40.97 | 41.29 | 41.63 | 41.95 | 42.63 |
| 80 | | 40.90 | 41.20 | 41.21 | 41.00 | 40.99 | 40.99 | 40.81 | 41.16 | 41.51 | 41.81 | 42.55 |
| 90 | | 40.88 | 41.18 | 41.29 | 41.23 | 40.85 | 40.97 | 40.87 | 41.05 | 41.51 | 42.08 | 42.68 |
| 100 | | 40.83 | 40.96 | 41.32 | 41.39 | 41.05 | 40.77 | 40.89 | 40.99 | 41.61 | 42.14 | 42.87 |
| 110 | | 40.76 | 40.98 | 41.15 | 41.27 | 41.04 | 41.02 | 41.13 | 41.13 | 41.57 | 42.40 | 43.25 |
| 120 | | | | | | | | | | | | |
| AVE. | 41.46 | 41.11 | | | | | | | | | | |
| C.V.(%) | 1.63 | 0.44 | | | | | | | | | | |
| ⊿ | 3.23 | 0.74 | | | | | | | | | | |

In the Table, AVE represents the average value, and C. V. (%) represents a rate of change, that is, (standard deviation/average value). Here, ⊿ represents a difference between the maximum value and the minimum value within the area.

Table 2 shows the average value (upper stage) of reflection factors of the respective areas as the result of the measurements of ten times and the deviations (lower stage) in reflection factor of the respective areas.

TABLE 2

| | 0 | 10 | 20 | 30 | 40 | 50 | 60 | 70 | 80 | 90 | 100 | 110 |
|---|---|---|---|---|---|---|---|---|---|---|---|---|
| REFLECTION FACTOR AVERAGE (N = 10) | | | | | | | | | | | | |
| 0 | | | | | | | | | | | | |
| 10 | | 41.08 | 41.05 | 41.44 | 41.23 | 41.20 | 41.22 | 41.40 | 41.86 | 42.21 | 42.99 | 44.09 |
| 20 | | 41.21 | 41.15 | 41.38 | 41.42 | 41.32 | 41.30 | 41.50 | 41.75 | 42.26 | 43.06 | 43.64 |
| 30 | | 41.10 | 41.29 | 41.34 | 41.50 | 41.39 | 41.35 | 41.33 | 41.60 | 42.04 | 42.80 | 43.53 |
| 40 | | 41.14 | 41.37 | 41.38 | 41.29 | 41.14 | 41.20 | 41.31 | 41.54 | 41.78 | 42.44 | 43.31 |
| 50 | | 41.05 | 41.32 | 41.37 | 41.24 | 41.02 | 41.13 | 41.09 | 41.40 | 41.62 | 42.27 | 43.00 |
| 60 | | 41.01 | 41.30 | 41.27 | 41.16 | 41.10 | 41.08 | 41.16 | 41.37 | 41.59 | 42.17 | 42.84 |
| 70 | | 40.98 | 41.18 | 41.25 | 41.19 | 41.11 | 40.96 | 41.11 | 41.38 | 41.72 | 42.05 | 42.75 |
| 80 | | 41.01 | 41.35 | 41.27 | 41.11 | 41.10 | 41.09 | 40.93 | 41.27 | 41.60 | 41.90 | 42.64 |
| 90 | | 41.05 | 41.33 | 41.42 | 41.29 | 41.00 | 41.06 | 40.96 | 41.15 | 41.60 | 42.18 | 42.79 |

TABLE 2-continued

| | 0 | 10 | 20 | 30 | 40 | 50 | 60 | 70 | 80 | 90 | 100 | 110 |
|---|---|---|---|---|---|---|---|---|---|---|---|---|
| 100 | | 41.02 | 41.11 | 41.44 | 41.47 | 41.17 | 40.88 | 41.00 | 41.09 | 41.73 | 42.25 | 42.96 |
| 110 | | 40.95 | 41.10 | 41.32 | 41.38 | 41.12 | 41.16 | 41.22 | 41.20 | 41.67 | 42.49 | 43.36 |
| 120 | | | | | | | | | | | | |

ALL AREAS 41.57

REFLECTION FACTOR DEVIATION C. V. (%)(N = 10)

| | 0 | 10 | 20 | 30 | 40 | 50 | 60 | 70 | 80 | 90 | 100 | 110 |
|---|---|---|---|---|---|---|---|---|---|---|---|---|
| 0 | | | | | | | | | | | | |
| 10 | | 0.758 | 0.687 | 0.629 | 0.567 | 0.540 | 0.613 | 0.557 | 0.551 | 0.580 | 0.615 | 0.625 |
| 20 | | 0.689 | 0.582 | 0.536 | 0.540 | 0.498 | 0.480 | 0.467 | 0.535 | 0.493 | 0.512 | 0.580 |
| 30 | | 0.608 | 0.588 | 0.510 | 0.469 | 0.409 | 0.400 | 0.386 | 0.376 | 0.416 | 0.417 | 0.486 |
| 40 | | 0.572 | 0.538 | 0.450 | 0.414 | 0.404 | 0.429 | 0.372 | 0.385 | 0.427 | 0.421 | 0.377 |
| 50 | | 0.566 | 0.524 | 0.429 | 0.386 | 0.402 | 0.404 | 0.394 | 0.455 | 0.422 | 0.417 | 0.420 |
| 60 | | 0.567 | 0.467 | 0.404 | 0.412 | 0.398 | 0.424 | 0.427 | 0.412 | 0.408 | 0.407 | 0.411 |
| 70 | | 0.530 | 0.542 | 0.396 | 0.426 | 0.417 | 0.424 | 0.427 | 0.388 | 0.433 | 0.411 | 0.423 |
| 80 | | 0.568 | 0.539 | 0.431 | 0.431 | 0.406 | 0.397 | 0.462 | 0.401 | 0.418 | 0.426 | 0.431 |
| 90 | | 0.516 | 0.567 | 0.438 | 0.427 | 0.430 | 0.433 | 0.433 | 0.420 | 0.419 | 0.405 | 0.427 |
| 100 | | 0.581 | 0.536 | 0.465 | 0.382 | 0.384 | 0.421 | 0.437 | 0.443 | 0.442 | 0.414 | 0.403 |
| 110 | | 0.650 | 0.588 | 0.571 | 0.459 | 0.392 | 0.401 | 0.414 | 0.422 | 0.422 | 0.440 | 0.442 |

In comparison with reflection factors in the respective areas from Table 1 and Table 2, the deviation is smallest in the vicinity of the light axis of the lens 8 (or a portion in which irradiation light rays of the LEDs 4 are converged most closely), and the deviation tends to become greater as the distance from this point becomes greater in the form of a concentric circle. It is considered that this tendency occurs because the amount of correction becomes greater as the distance from the light axis becomes longer.

Moreover, in the case when the reflection factor is measured by using the area sensor, there is a considerable difference between reflection factors obtained separately in the respective areas, even when a measuring object that is supposed to have even density is measured. The reason for this is because the light-irregularity correction precision differs depending on positions, and because density irregularities originally contained in the measuring object give adverse effects.

(Simultaneous Reproducibility 2)

Pieces of ND paper having different reflection factors were placed within the same image, and the simultaneous reproducibility, obtained in the case when the ratio of the density values of these is calculated as a reflection factor, was examined. The following description will discuss the sequence of the processes.

(1) The current value of the LEDs 4 is set to 0 mA, and a dark (offset) image is picked up.

(2) A plate, formed by bonding pieces of paper of ND 9.5 (actual value of reflection: factor 87.00%) and ND 6.5 (actual value of reflection factor. 36.21%) onto a base plate with each of these entering half of the image angle, is prepared, and an image thereof is picked up ten times.

Figure 10:
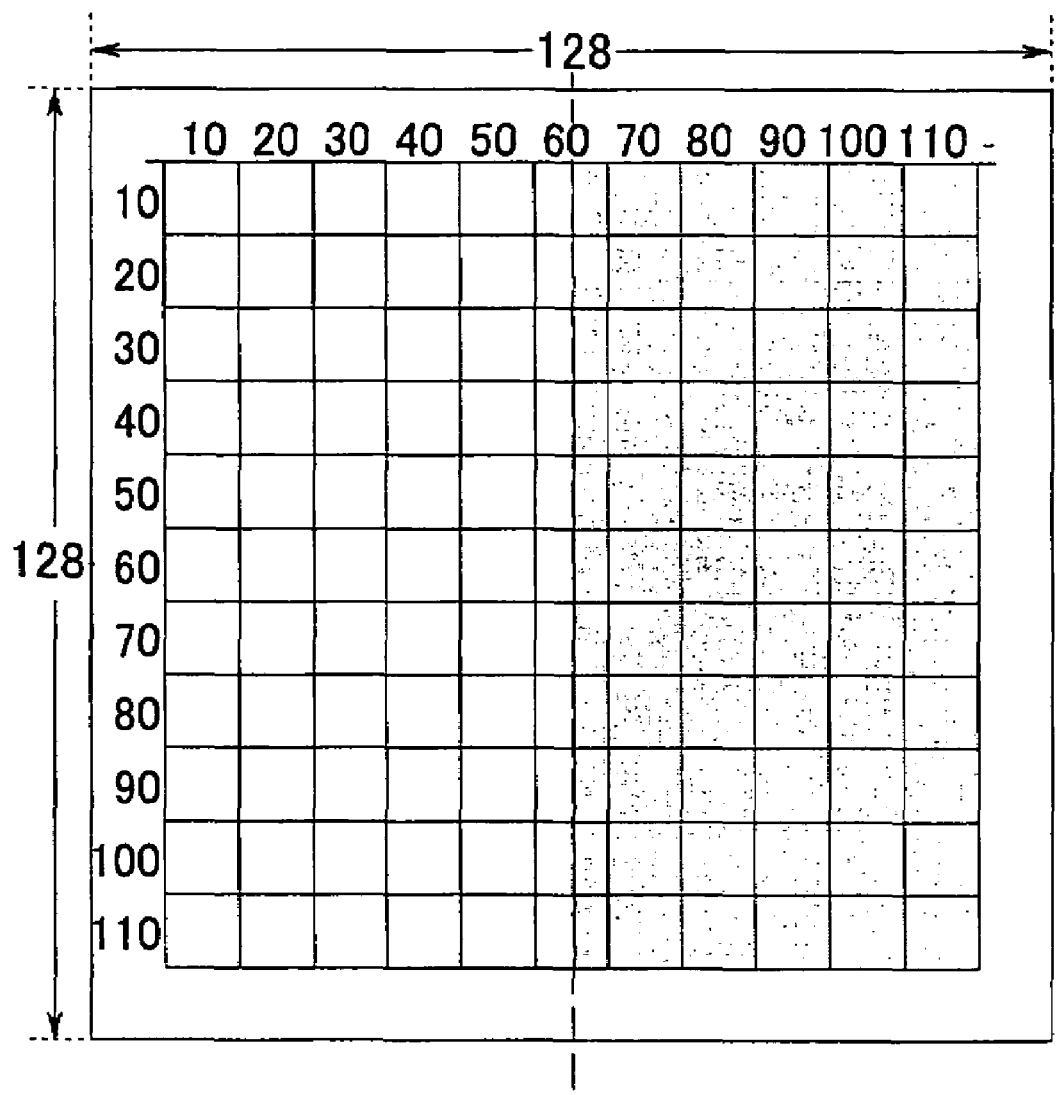
FIG. 10 is a plan view that shows another example in which one sheet of an image is divided into 11×11 areas.

(3) After light irregularities of the respective pixels have been corrected, one sheet of image is divided into 11×11 areas (each area containing 10×10=100 pixels) as shown in FIG. 10, and the average value of the quantities of light of the respective areas is calculated. The ratio of ND 9.5 and ND 6.5 of this average value of quantities of light is used as a reflection factor so that the reflection factors of the respective areas are calculated.

Table 3 shows the results of measurements of one time among the measurements carried out ten times. The left side on the upper stage of Table 3 shows the average of light quantities of the respective areas relating to ND 9.5, and the right side on the upper stage thereof shows the average of light quantities of the respective areas relating to ND 6.5. The left side on the lower stage shows a case in which, supposing that a portion at which ND 9.5 and ND 6.5 intersect with each other within the image is a center line, a ratio that is found based upon this line in a line-symmetrical manner is used as a reflection factor (referred to as symmetrical reflection factor). Moreover, the right side on the lower stage shows a case in which the area is divide into areas of ND 9.5 and ND 6.5 by the center line, with the ratio of the respectively identical areas (for example: area of lateral axis 10 and area of lateral axis 50, area of lateral axis 50 and area of lateral axis 110) being used as a reflection factor (referred to as one-directional reflection factor).

TABLE 3

| | | LIGHT QUANTITY BLOCK AVERAGE DISTRIBUTION | | | | | | | | | |
|---|---|---|---|---|---|---|---|---|---|---|---|
| No.1 | 10 | 20 | 30 | 40 | 50 | 60 | 70 | 80 | 90 | 100 | 110 |
| 10 | 0.997 | 0.999 | 1.001 | 0.996 | 0.990 | | 0.458 | 0.458 | 0.460 | 0.467 | 0.474 |
| 20 | 0.995 | 0.994 | 0.994 | 0.995 | 0.989 | | 0.455 | 0.455 | 0.458 | 0.463 | 0.468 |
| 30 | 0.992 | 0.990 | 0.991 | 0.993 | 0.990 | | 0.453 | 0.451 | 0.452 | 0.459 | 0.464 |
| 40 | 0.994 | 0.991 | 0.991 | 0.992 | 0.989 | | 0.452 | 0.450 | 0.450 | 0.455 | 0.461 |
| 50 | 0.990 | 0.990 | 0.993 | 0.992 | 0.988 | | 0.449 | 0.449 | 0.448 | 0.453 | 0.458 |
| 60 | 0.992 | 0.991 | 0.993 | 0.990 | 0.989 | | 0.449 | 0.447 | 0.448 | 0.451 | 0.455 |
| 70 | 0.991 | 0.989 | 0.995 | 0.994 | 0.991 | | 0.447 | 0.447 | 0.448 | 0.150 | 0.453 |
| 80 | 0.990 | 0.992 | 0.996 | 0.994 | 0.990 | | 0.448 | 0.447 | 0.447 | 0.450 | 0.455 |
| 90 | 0.992 | 0.991 | 0.998 | 0.997 | 0.992 | | 0.448 | 0.446 | 0.447 | 0.451 | 0.454 |
| 100 | 0.994 | 0.992 | 1.001 | 1.001 | 0.997 | | 0.448 | 0.445 | 0.448 | 0.451 | 0.456 |
| 110 | 0.995 | 0.993 | 0.997 | 1.001 | 0.996 | | 0.448 | 0.445 | 0.448 | 0.452 | 0.460 |

TABLE 3-continued

|  | C.V. (%) | 0.33 |
|---|---|---|
|  |  | 0.013 |

|  | C.V. (%) | 1.40 |
|---|---|---|
|  |  | 0.030 |

SYMMETRICAL REFLECTION FACTOR

| No. 1 | 10/110 | 20/100 | 30/90 | 40/80 | 50/70 |
|---|---|---|---|---|---|
| 10 | 47.58 | 46.78 | 45.98 | 46.01 | 46.31 |
| 20 | 47.02 | 46.64 | 46.12 | 45.73 | 45.98 |
| 30 | 46.73 | 46.36 | 45.64 | 45.35 | 45.73 |
| 40 | 46.38 | 45.87 | 45.40 | 45.40 | 45.69 |
| 50 | 46.21 | 45.73 | 45.10 | 45.28 | 45.46 |
| 60 | 45.91 | 45.47 | 45.06 | 45.12 | 45.41 |
| 70 | 45.77 | 45.54 | 45.08 | 45.00 | 45.12 |
| 80 | 45.94 | 45.38 | 44.92 | 44.96 | 45.19 |
| 90 | 45.81 | 45.46 | 44.82 | 44.74 | 45.12 |
| 100 | 45.86 | 45.44 | 44.77 | 44.44 | 44.93 |
| 110 | 46.20 | 45.54 | 44.87 | 44.42 | 45.00 |

|  | AVE. | 45.60 | 45.29 |
|---|---|---|---|
|  | C.V. (%) | 1.42 | 0.63 |
|  |  | 3.17 | 0.95 |

ONE-DIRECTIONAL REFLECTION FACTOR

|  | 10/70 | 20/80 | 30/90 | 40/100 | 50/110 |
|---|---|---|---|---|---|
| 10 | 45.96 | 45.89 | 45.98 | 46.90 | 47.94 |
| 20 | 45.71 | 45.81 | 46.12 | 46.56 | 47.29 |
| 30 | 45.64 | 45.49 | 45.64 | 46.22 | 46.83 |
| 40 | 45.47 | 45.45 | 45.40 | 45.83 | 46.60 |
| 50 | 45.36 | 45.39 | 45.10 | 45.61 | 46.30 |
| 60 | 45.28 | 45.07 | 45.06 | 45.52 | 46.04 |
| 70 | 45.13 | 45.23 | 45.08 | 45.31 | 45.77 |
| 80 | 45.21 | 45.06 | 44.92 | 45.28 | 45.92 |
| 90 | 45.13 | 44.98 | 44.82 | 45.21 | 45.80 |
| 100 | 45.06 | 44.83 | 44.77 | 45.05 | 45.73 |
| 110 | 45.02 | 44.79 | 44.87 | 45.16 | 46.18 |

|  | AVE. | 45.60 | 45.29 |
|---|---|---|---|
|  | C.V. (%) | 1.45 | 0.55 |
|  |  | 3.17 | 0.91 |

Table 4 shows the average value (upper stage) and deviation (lower staged) obtained by carrying out calculations as shown on the lower stage of Table 3 corresponding to measurements of ten times.

TABLE 4

SYMMETRICAL REFLECTION FACTOR AVERAGE (N = 10)

|  | 10/110 | 20/100 | 30/90 | 40/80 | 50/70 |
|---|---|---|---|---|---|
| 10 | 47.54 | 46.77 | 46.05 | 46.02 | 46.32 |
| 20 | 47.05 | 46.67 | 46.10 | 45.73 | 46.01 |
| 30 | 46.78 | 46.33 | 45.66 | 45.36 | 45.71 |
| 40 | 46.37 | 45.88 | 45.44 | 45.44 | 45.68 |
| 50 | 46.24 | 45.72 | 45.11 | 45.29 | 45.43 |
| 60 | 45.90 | 45.48 | 45.07 | 45.15 | 45.42 |
| 70 | 45.82 | 45.57 | 45.08 | 45.04 | 45.13 |
| 80 | 45.93 | 45.40 | 44.95 | 44.98 | 45.20 |
| 90 | 45.85 | 45.46 | 44.82 | 44.73 | 45.15 |
| 100 | 45.88 | 45.45 | 45.75 | 44.44 | 44.93 |
| 110 | 46.19 | 44.58 | 45.84 | 44.42 | 44.98 |

| ALL AREAS | 45.61 | C.V. (%) | 1.42 | 0.63 |
|---|---|---|---|---|
|  |  |  | 3.12 | 0.94 |

ONE-DIRECTIONAL REFLECTION FACTOR AVERAGE (N = 10)

|  | 10/70 | 20/80 | 30/90 | 40/100 | 50/110 |
|---|---|---|---|---|---|
| 10 | 45.95 | 45.91 | 46.05 | 46.88 | 47.92 |
| 20 | 45.74 | 45.82 | 46.10 | 46.59 | 47.34 |
| 30 | 45.63 | 45.51 | 45.66 | 46.18 | 46.86 |
| 40 | 45.47 | 45.49 | 45.44 | 45.83 | 46.59 |
| 50 | 45.34 | 45.40 | 45.11 | 45.61 | 46.33 |
| 60 | 45.28 | 45.11 | 45.07 | 45.52 | 46.05 |
| 70 | 45.14 | 45.26 | 45.08 | 45.35 | 45.81 |
| 80 | 45.21 | 45.07 | 44.95 | 45.31 | 45.92 |
| 90 | 45.15 | 44.97 | 44.82 | 45.22 | 45.85 |
| 100 | 45.06 | 44.83 | 44.75 | 45.05 | 45.75 |
| 110 | 45.01 | 44.82 | 44.84 | 45.18 | 46.16 |

| ALL AREAS | 45.61 | C.V. (%) | 1.45 | 0.54 |
|---|---|---|---|---|
|  |  |  | 3.17 | 0.89 |

SYMMETRICAL REFLECTION FACTOR C. V (%) (N = 10)

|  | 10/110 | 20/100 | 30/90 | 40/80 | 50/70 |
|---|---|---|---|---|---|
| 10 | 0.37 | 0.36 | 0.34 | 0.34 | 0.35 |
| 20 | 0.34 | 0.29 | 0.25 | 0.25 | 0.26 |
| 30 | 0.24 | 0.23 | 0.21 | 0.24 | 0.22 |
| 40 | 0.23 | 0.26 | 0.23 | 0.20 | 0.20 |
| 50 | 0.22 | 0.22 | 0.22 | 0.22 | 0.20 |
| 60 | 0.22 | 0.19 | 0.19 | 0.21 | 0.19 |
| 70 | 0.23 | 0.17 | 0.21 | 0.21 | 0.19 |
| 80 | 0.20 | 0.22 | 0.18 | 0.22 | 0.20 |
| 90 | 0.24 | 0.21 | 0.23 | 0.22 | 0.20 |
| 100 | 0.23 | 0.24 | 0.22 | 0.23 | 0.20 |

ONE-DIRECTIONAL REFLECTION FACTOR C. V (%) (N = 10)

| 10/70 | 20/80 | 30/90 | 40/100 | 50/110 |
|---|---|---|---|---|
| 0.31 | 0.33 | 0.34 | 0.37 | 0.41 |
| 0.24 | 0.24 | 0.25 | 0.31 | 0.36 |
| 0.20 | 0.25 | 0.21 | 0.22 | 0.26 |
| 0.21 | 0.20 | 0.23 | 0.25 | 0.22 |
| 0.19 | 0.22 | 0.22 | 0.22 | 0.22 |
| 0.18 | 0.21 | 0.19 | 0.19 | 0.22 |
| 0.22 | 0.20 | 0.21 | 0.18 | 0.21 |
| 0.19 | 0.22 | 0.18 | 0.22 | 0.21 |
| 0.20 | 0.23 | 0.23 | 0.21 | 0.24 |
| 0.19 | 0.23 | 0.22 | 0.24 | 0.25 |

TABLE 4-continued

| 110 | 0.24 | 0.25 | 0.23 | 0.21 | 0.21 | 0.18 | 0.21 | 0.23 | 0.24 | 0.26 |
|---|---|---|---|---|---|---|---|---|---|---|
| | ALL AREAS | 0.23 | | | | | ALL AREAS | 0.23 | | |

In comparison with the results of simultaneous reproducibility 1, the result of simultaneous reproducibility 2 provide values that are approximately two times superior in C. V. (%) (rate of change: standard deviation/average value). The reason for this is because, in the measurements of simultaneous reproducibility 1, the measuring subjects need to be exchanged with the hands for each of the measurements, while, in the measurements of simultaneous reproducibility 2, it is not necessary to touch the measuring subjects with the hands. In other words, the results of simultaneous reproducibility 2 are considered to be close to the inherent image-pickup reproducibility of the CMOS area sensor.

(Reflection Factor Linearity)

A known spectrophotometer (MINOLTA CM-503c: using no area sensor) whose precision had been controlled was used to measure plurality of kinds of ND paper having different reflection factors so that the correlation with the reflection factor measuring device of the embodiment of the present invention was examined.

The reflection factors of a plurality of kinds of ND paper to be used were preliminarily measured by using the spectrophotometer. The reflection factors were measured at randomly selected five points on the ND paper, and the average value was used.

(1) The current value of the LEDs 4 is set to 0 mA, and a dark (offset) image is picked up.

(2) An image of the ND paper that has been preliminarily measured by the spectrophotometer is picked up.

(3) Light-irregularity correction processes are carried out on five points (pixels) on each image that are evenly distributed as shown in FIG. 6.

Figure 11:
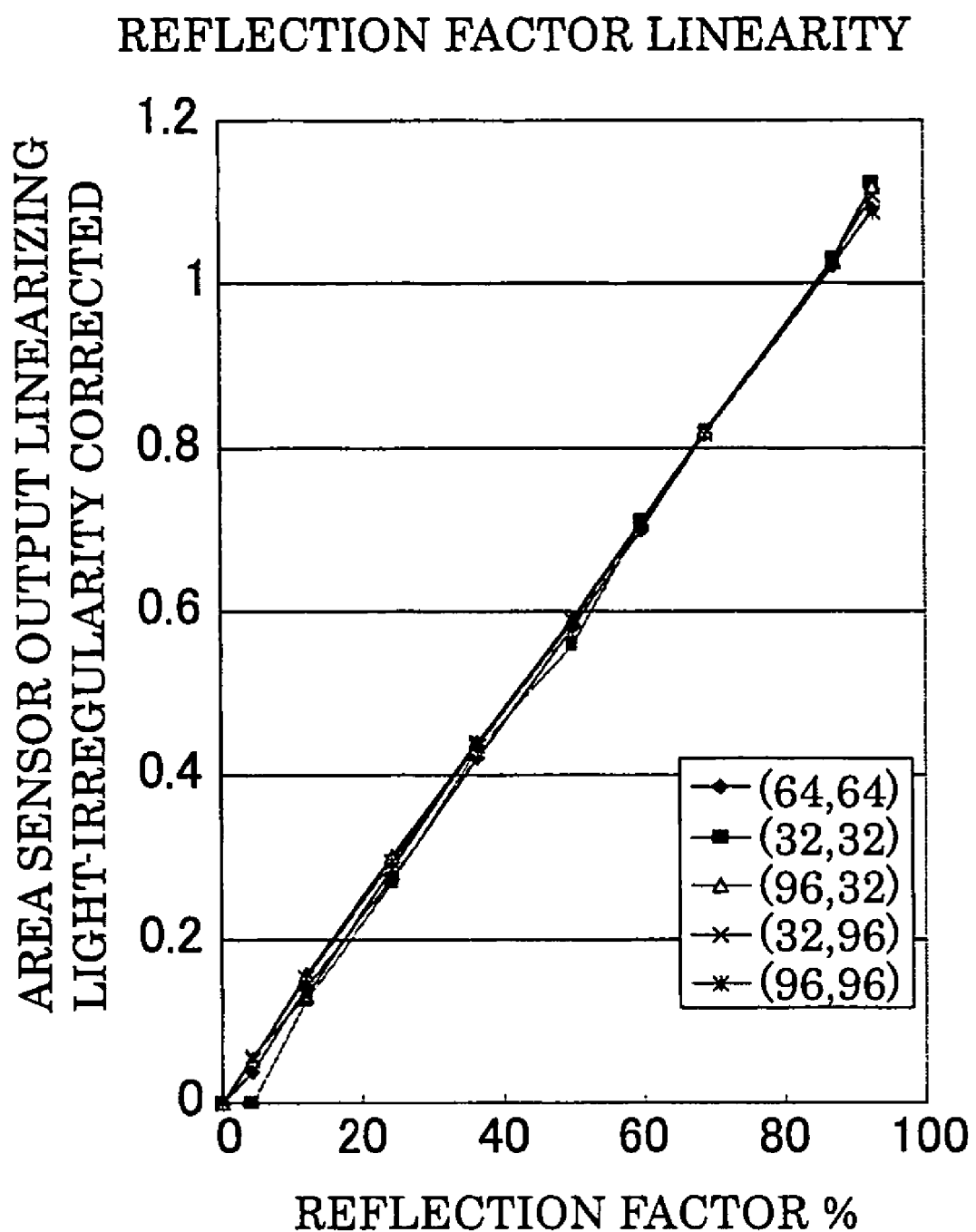
FIG. 11 is a drawing that shows a state in which 5 points of each image shown in FIG. 6 have been subjected to light-irregularity corrections, and plotted.

FIG. 11 shows a graph in which values measured by the spectrophotometer are plotted on the axis of abscissas, while the five points (pixels) of each image shown in FIG. 6 are light-irregularity-corrected by the present invention and the resulting values are plotted on the axis of ordinates.

The results shown in the graph of FIG. 11 are obtained not on an area average basis, but on a pixel unit basis; however, pixel point 3 (96, 32) or the like close to the light axis has good linearity. Point 1 (32, 32) is a pixel that exhibits the darkest value among the five pixels (with respect to raw data), with the poorest linearity among the five pixels. These experiments also show that it is difficult to carry out the light-irregularity correction on portions separated from the light axis.

(Temperature Characteristics)

Measurements were carried out so as to confirm the temperature characteristics of the reflection-factor measuring device of the present embodiment.

The following operations were carried out after the system (with the power switch being turned on) had sufficiently adapted to respective environments at 10° C., 20° C. and 30° C. A member, formed by bonding ND 9.5 (reflection factor actual measured value 87.00%) and ND 6.5 (reflection factor actual measured value 36.21%) to a base plate with each of these entering half of the image angle, was used as a measuring object.

(1) The current value of the LEDs 4 is set to 0 mA, and a dark (offset) image is picked up.

(2) The current value of the LEDs 4 is set to (10° C.: 16.52 (mA), 20° C.: 17.20 (mA), 30° C.: 17.95 (mA)) at the respective environment temperatures, and the sequence enters a stand-by state waiting for the LEDs light quantity to be detected by the photodetector 10 to exceed the respective values (10° C.: 0.788(V), 20° C.: 0.786(V), 30° C.: 0.783 (V)).

(3) Immediately after the conditions of (2) have been satisfied, images are picked up. The above-mentioned operations are repeated ten times.

Table 5 shows the results of all-area average reflection factor at each of the temperatures obtained by the respective measurements of ten times. Here, S.D. represents the standard deviation.

TABLE 5

AVERAGE REFLECTION FACTOR (%) TEMPERATURE CHARACTERISTICS

| | ENVIRONMENT TEMPERATURE | | |
|---|---|---|---|
| | 10° C. | 20° C. | 30° C. |
| No. 1 | 45.09 | 45.24 | 45.64 |
| No. 2 | 44.94 | 45.31 | 45.77 |
| No. 3 | 45.44 | 45.10 | 45.61 |
| No. 4 | 45.16 | 45.30 | 45.58 |
| No. 5 | 45.02 | 45.21 | 45.38 |
| No. 6 | 44.81 | 45.08 | 45.72 |
| No. 7 | 45.01 | 45.39 | 45.50 |
| No. 8 | 45.15 | 45.16 | 45.73 |
| No. 9 | 45.06 | 45.45 | 45.53 |
| No. 10 | 44.82 | 45.41 | 45.59 |
| AVE. | 45.05 | 45.26 | 45.60 |
| S.D. | 0.184 | 0.129 | 0.118 |
| C.V.(%) | 0.41 | 0.29 | 0.26 |
| Δ | 0.63 | 0.37 | 0.39 |

The results show that there are hardly any influences caused by environment temperatures, and the temperature tendency is approximately 0.28 (%/10° C.)

(Drift Characteristics)

Measurements were carried out so as to confirm the drift tendency of the reflection factor measuring device of the present embodiment in the applied state (including time and temperature).

(1) Thermocouples are attached to main units (the inside of the driving circuit 20, the vicinity of the LEDs 4, the vicinity of the area sensor 8) of the reflection factor measuring device of the embodiment so as to monitor the temperature.

(2) The reflection factor measuring device is allowed to sufficiently adapt to the environment with the power-supply being turned off.

(3) The current value of the LEDs 4 is set to 0 mA, and a dark (offset) image is picked up.

(4) The current value of the LEDs 4 is set to 17.3 (mA), and the sequence enters a stand-by state waiting for the LEDs light quantity to be detected by the photodetector 10 to exceed 0.789 (V).

(5) Immediately after the above-mentioned condition (2) has been satisfied, image-pickup operations are carried out three times.

(6) The processes of (3) to (5) are repeated every 10 minutes, until all the monitoring unit temperatures have entered an equilibrium state.

Figure 12:
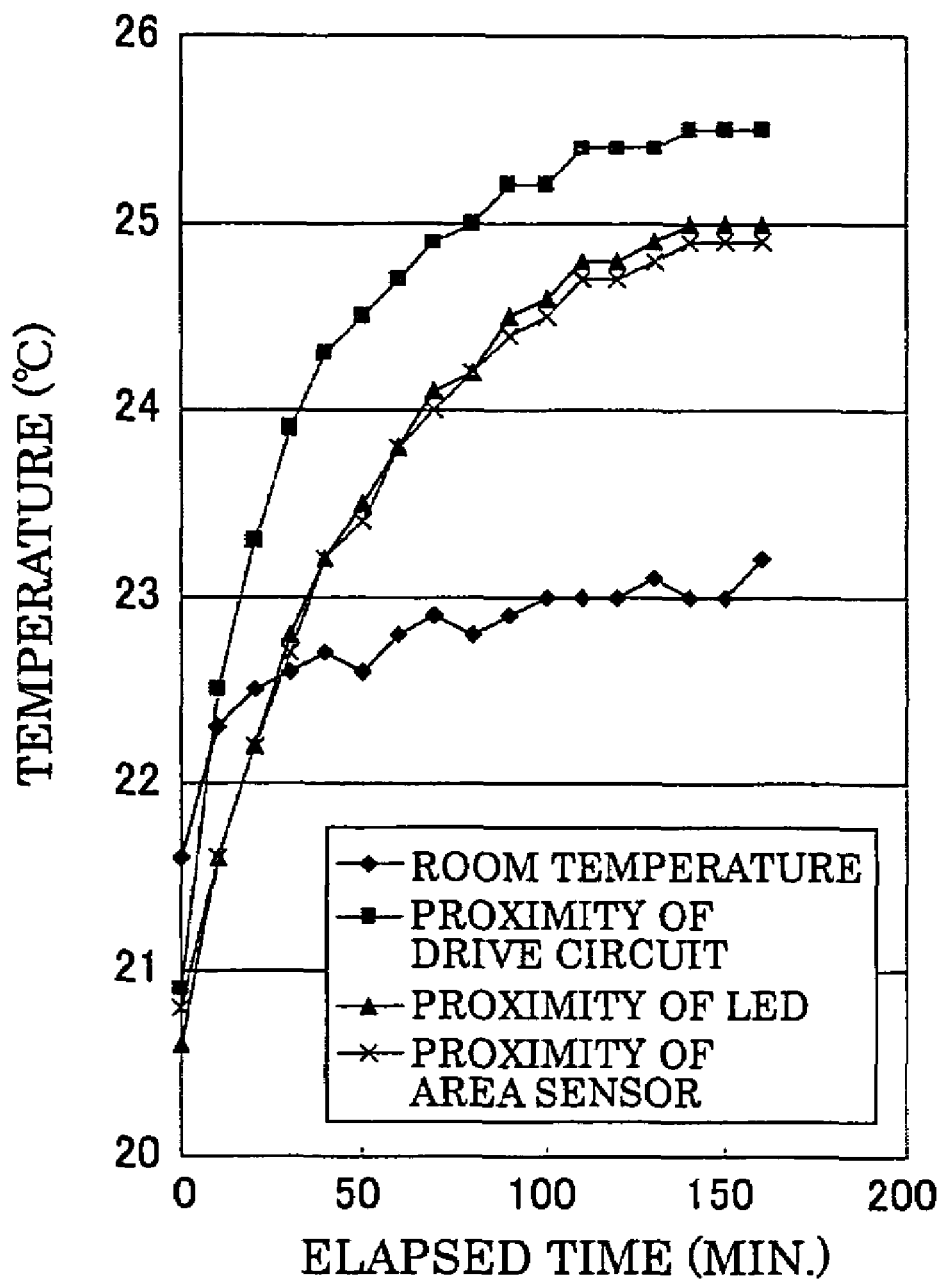
FIG. 12 is a drawing that shows the relationship between the elapsed time and temperature in main units of a reflection-factor measuring device of an embodiment

The graph of FIG. 12 shows the relationship between the elapsed time (every 10 minutes) and the temperature in the main units (the vicinity of the drive circuit 20, the vicinity of the LEDs 4, the vicinity of the area sensor 8) of the reflection factor measuring device of the embodiment.

Figure 13:
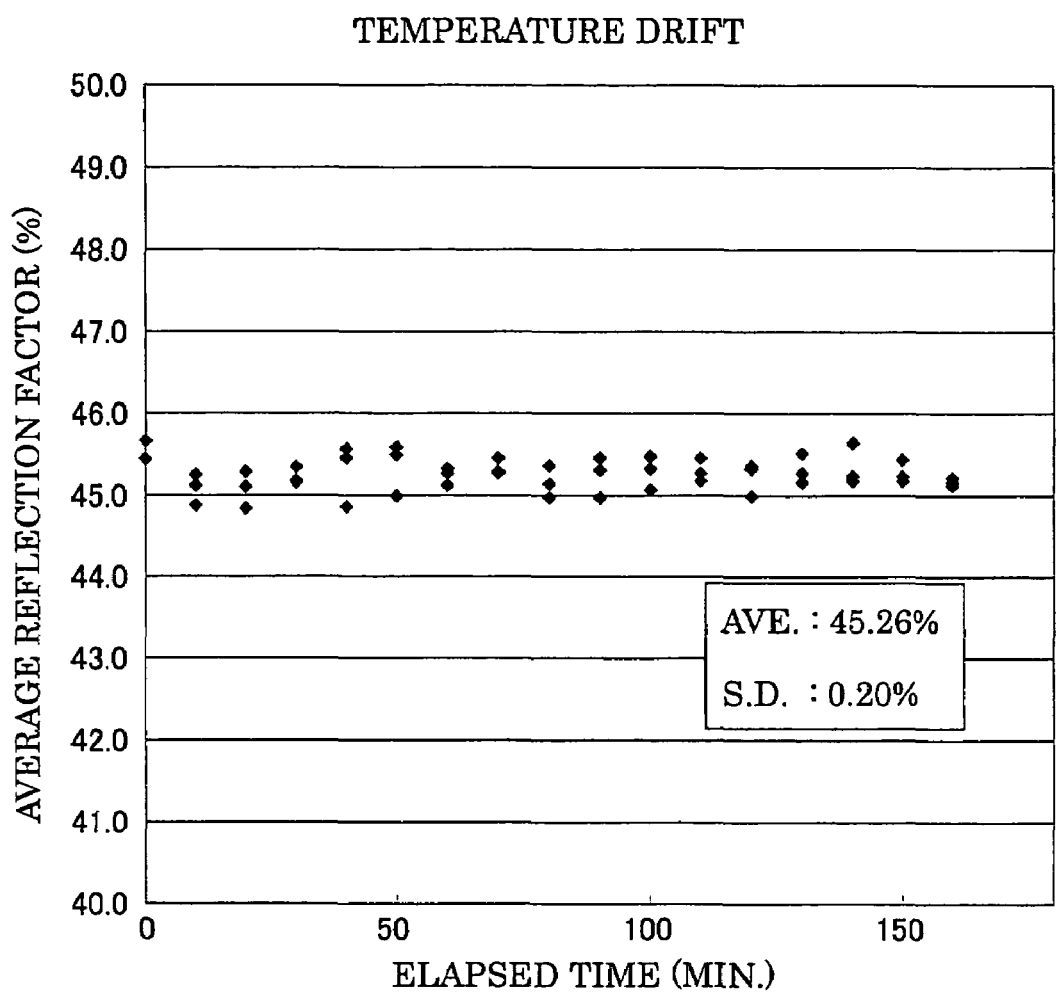
FIG. 13 is a drawing in which the results of measurements carried out on the reflection factor three times every 10 minutes.

FIG. 13 shows a graph in which the resulting reflection factors, obtained by carrying out measurements three times every 10minutes, are plotted.

From the results of FIG. 12 and FIG. 13, no drift phenomenon is confirmed in the applied state (including temperature and time), and even if there is some, the degree thereof is so small that it is included in deviations occurring in each simultaneous measuring process.

As a result of the above-mentioned examination, in the reflection factor measuring device of the present embodiment, it is confirmed that C. V.=0.23% (in the vicinity of a reflection factor of 45%) with respect to the simultaneous reproducibility (n=10),0.28 (%/10° C.) in the vicinity of a reflection factor of 45% with respect to the temperature characteristics and there is hardly any drift tendency in the applied state (including time and temperature).

It is found that the CMOS area sensor used in the present embodiment may be sufficiently applied to measurements in a semi-determination level of a measuring device for urine test paper and the like.

Embodiment 2

Figure 14:
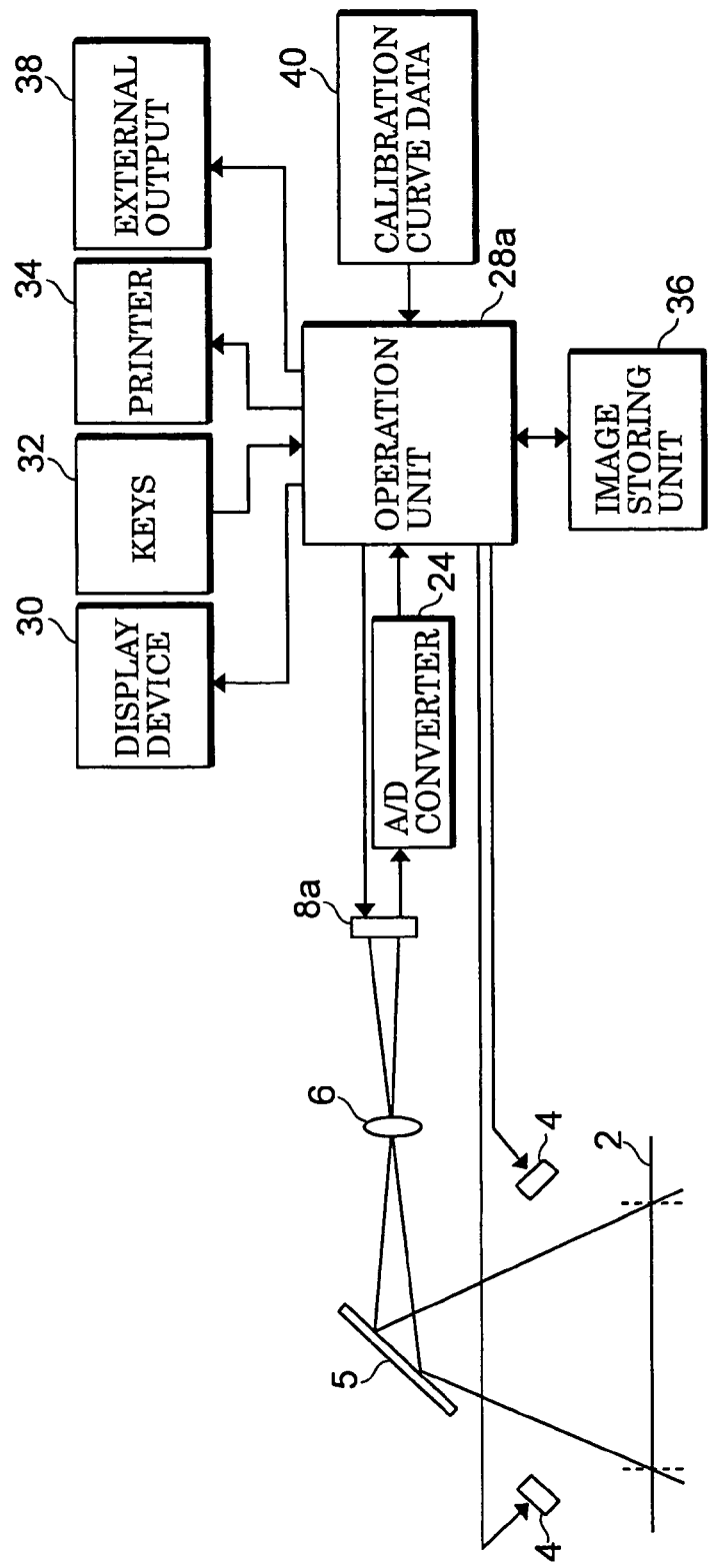
FIG. 14 is a schematic structural drawing that shows another example of the reflection-factor measuring device to which the present invention is applied.

With respect to a second embodiment, FIG. 14 schematically shows one example of a two-dimensional reflection-factor measuring device to which an output correction method in accordance with the second aspect of the present invention is applied with an area sensor being used as a sensor.

In comparison with the reflection factor measuring device of FIG. 1, the present device is different in that a photodetector 10 for monitoring the quantity of light is not installed. The other structure is basically the same. Reflected light of a measuring object 2 is converged on an area sensor 8a as an image by a lens 6 through a reflection plate 5. The area sensor 8a includes devices up to the amplifier 22 shown in FIG. 1. The detection signal of the area sensor 8a is taken into a calculation unit 28a through an A/D converter 24. This calculation unit 28a corresponds to the RAM 26 and the personal computer 28 in FIG. 1. A display device 30, a keyboard 32 and a printer 34 are connected to the calculation unit 28a. Reference numeral 36 represents an image storing unit for storing acquired image data, which is constituted by, for example, a hard disk device. Calibration curve data 40, which is used for converting the reflection factor calculated by the calculation unit 28a to density, is stored in the hard disk device or a floppy disk device.

The results of the data processing in the calculation unit 28a are taken out to a necessary external device as an external output 38.

In this embodiment, in order to acquire the relationship between the output of the area sensor 8a and the reflection factor of the measuring object 2 as linearizing data, a reference plate having a known reflection factor is measured as the measuring object 2. With respect to the standard plates, pieces of ND paper are used, and those of 11 stages are prepared ranging one plate having the greatest reflection factor to another plate having the smallest reflection factor.

Figure 15:
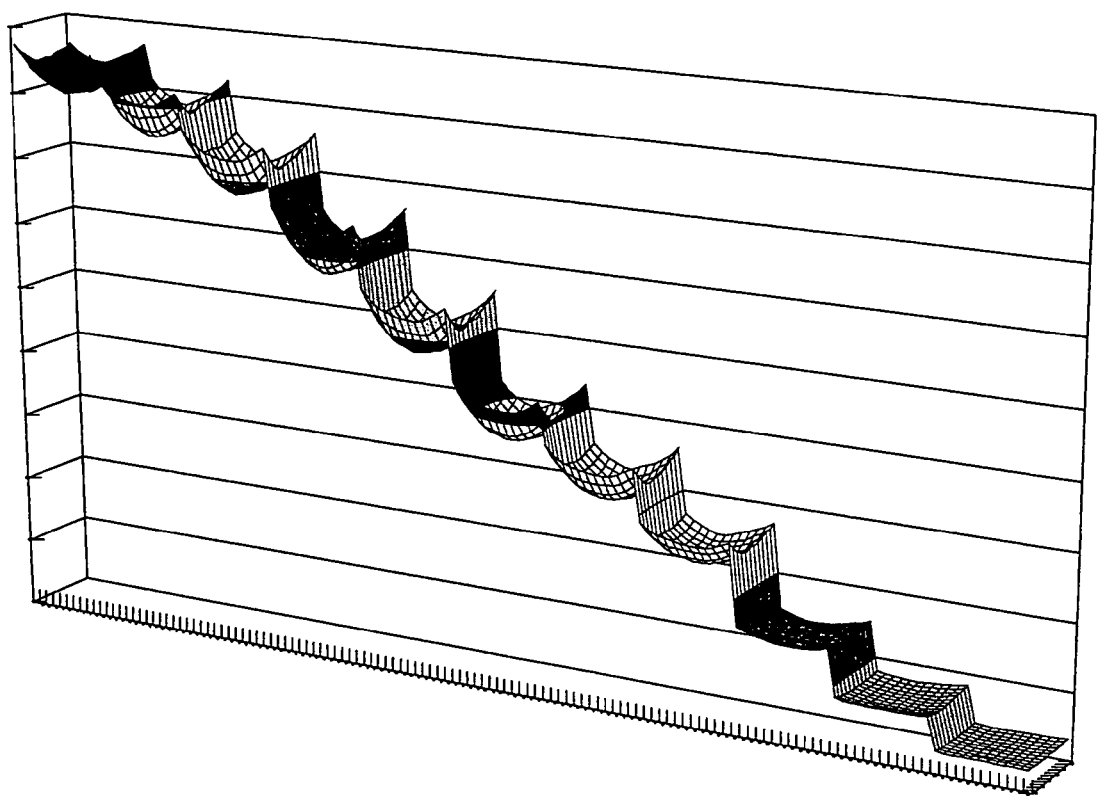
FIG. 15 is a drawing that shows the results of measurements carried out on standard plates having different reflection factors in the second embodiment together with the outputs of the area sensor.

FIG. 15 shows the results of measurements using those standard plates as the measuring object 2 together with the output of the area sensor 8a. The axis of ordinates represents the output, and the axis of abscesses represents the respective standard plates that are successively aligned in a descending order in the reflection factor. Since the output data of each standard plate has not been subjected to light-irregularity correcting processes, it has a curved shape.

Figure 16:
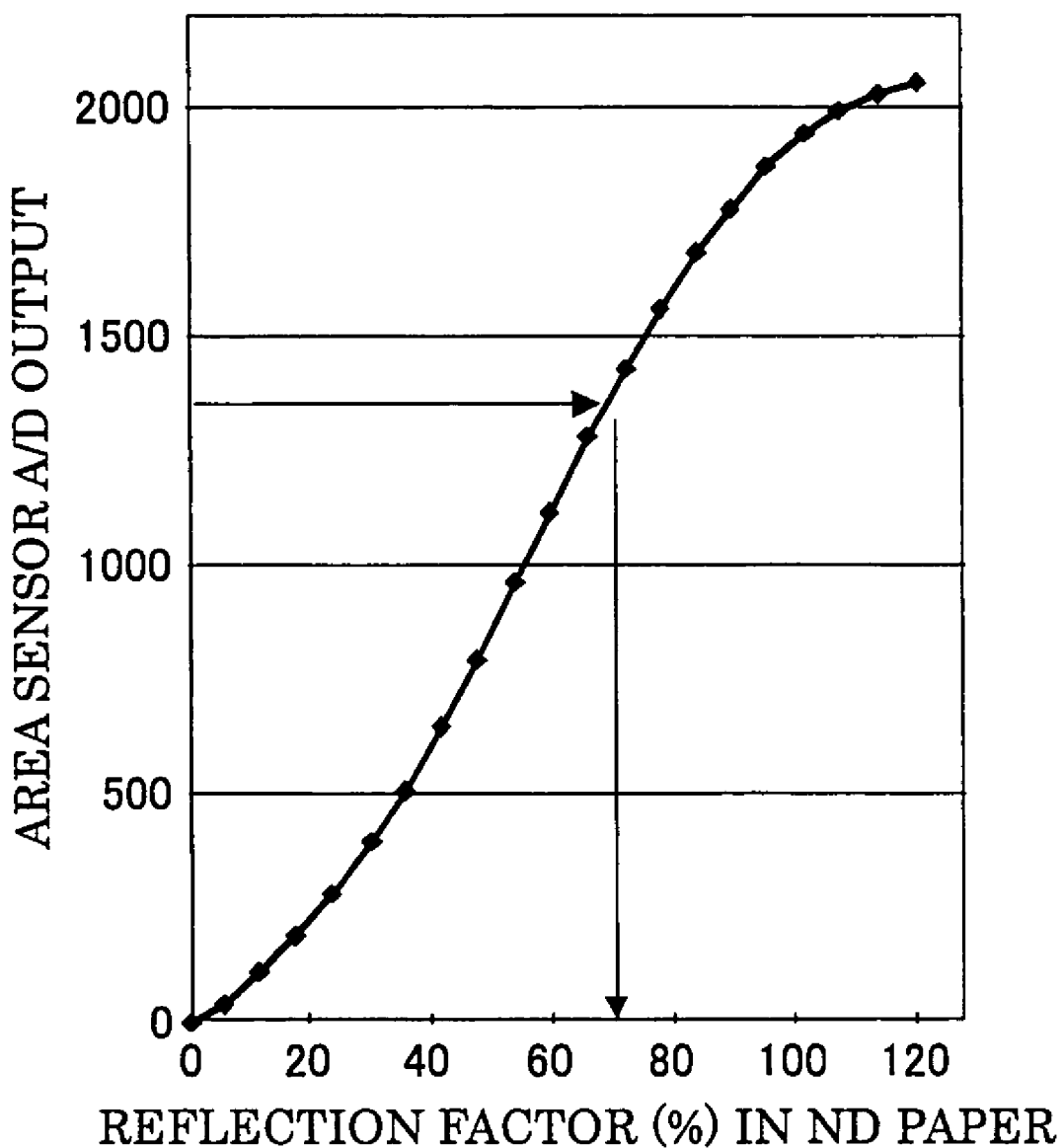
FIG. 16 is a drawing that shows the results of FIG. 15 with respect to one pixel of the area sensor.

FIG. 16 shows the relationship between the reflection factor and the output with respect to one pixel of the area sensor 8a. The axis of ordinates represents the output of the area sensor 8a, and the axis of abscissas represents known reflection factors of the standard plates. Since the output of the area sensor 8a has a non-linear property with respect to the quantity of received light, this curve exhibits an S-letter shape, which indicates the same characteristics as those shown in FIG. 3.

With respect to each pixel of the area sensor 8a, data as shown in FIG. 16 is stored as linearizing data for each pixel.

In the case when a sample whose reflection factor is unknown is measured, by using linearizing data for each of the pixels, the reflection factor is found from its output as shown by arrows in FIG. 16. The reflection factor is obtained by interpolating gaps between the actually measured points of the linearizing data.

The reflection factor of the unknown sample thus obtained is allowed to form reflection factor data in which irradiation irregularities due to a light source and non-linear properties of the lens and the area sensor 8a have been corrected, thereby preparing reflection-factor-related data having linearity.

Figure 17:
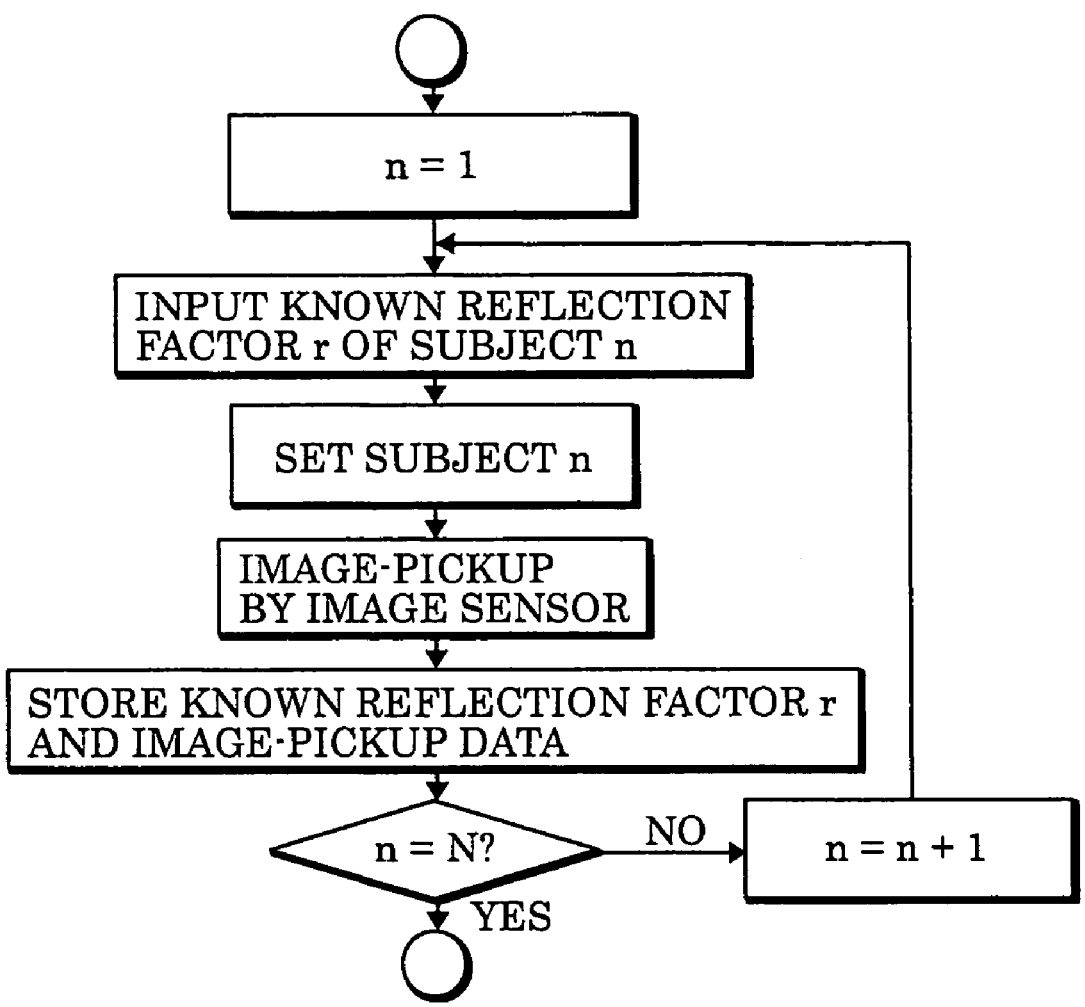
FIG. 17 is a flow chart that shows a sequence of processes to be carried out to obtain linearizing data in the second embodiment
Figure 18:
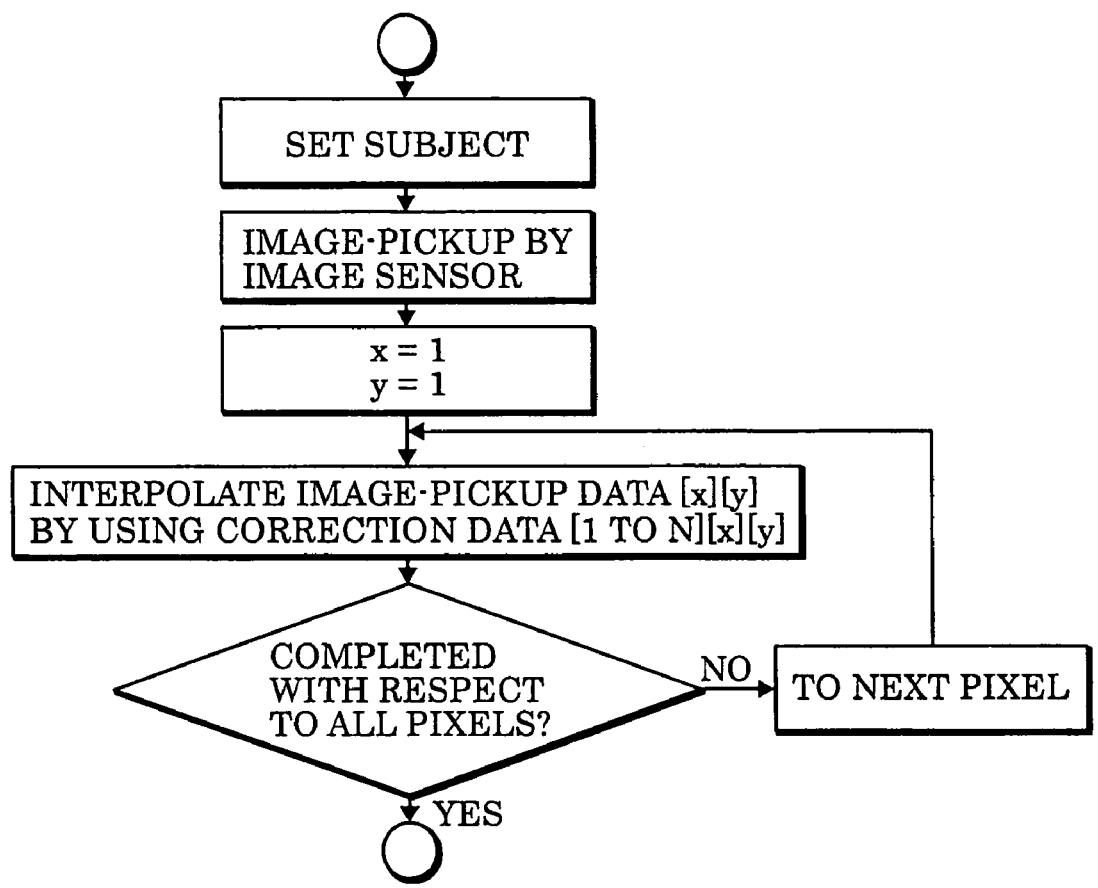
FIG. 18 is a flow chart that shows a sequence of reflection-factor measuring processes to be carried out on an unknown sample.

Referring to FIG. 17 and FIG. 18, the following description will further discuss these operations.

FIG. 17 shows a sequence used for obtaining linearizing data. Here, N-number of kinds of plates having different reflection factors are prepared as reference plates. In other words, 11 kinds that have varied reflection factors ranging from 100% to 0% on a 10% unit basis are prepared. One reference plate is placed at the position of the measuring object 2, and an image thereof is picked up by the area sensor 8a. At this time, the known reflection factor r and image-pickup data of the reference plate are stored. These operations are repeated with respect to all the reference plates.

Thus, the linearizing data of FIG. 16 that indicates the relationship between the output and the reflection factor of each pixel of the image-pickup data is obtained for each of the pixels.

In the operations shown in FIG. 18, a sample whose reflection factor is unknown is placed at the position of the measuring object, and an image thereof is picked up by the area sensor 8a. Based upon the results of the picked up image, with respect to the coordinates (x, y) indicating the pixel position, the reflection factor is found from the output data of each pixel, in a manner as indicated by arrows in FIG. 16. These operations are carried out with respect to all the pixels.

Embodiment 3

With respect to a third embodiment, the following description will discuss an output correction method in accordance with the third aspect of the present invention in which an area sensor is used as its sensor.

Here, the reflection factor measuring device to be used is the same as that shown in FIG. 14.

In this embodiment, the area sensor 8a is designed so that the exposing time during which the area sensor 8a receives light is programmable. With respect to such an area sensor, for example, a CMOS image sensor (H64283FP) made by Mitsubishi Electric Corporation, which is used in the embodiment shown in FIG. 1, may be used. However, not limited to CMOS image sensors, a CCD image sensor may be used as the area sensor 8a as long as it makes the exposing time programmable.

Although the output of the area sensor 8a does not have linearity with respect to the quantity of received light, the quantity of received light is directly proportional to the exposing time. Here, the quantity of received light is directly proportional to the reflection factor; therefore, even in the case of using a single reference plate, that is, a common reference plate, by changing the exposing time, it becomes possible to obtain the same results as the measurements using reference plates having different reflection factors.

A white plate serving as a reference plate is placed at the position of the measuring object 2 in FIG. 14. First, measurements are carried out by using reference exposing time. Next, while the white plate serving as the measuring object is maintained in the same state, the same measurements are carried out while the exposing time is reduced to 90% of the reference exposing time. In the same manner, the exposing time is reduced to 80%, 70% and so on.

Figure 19:
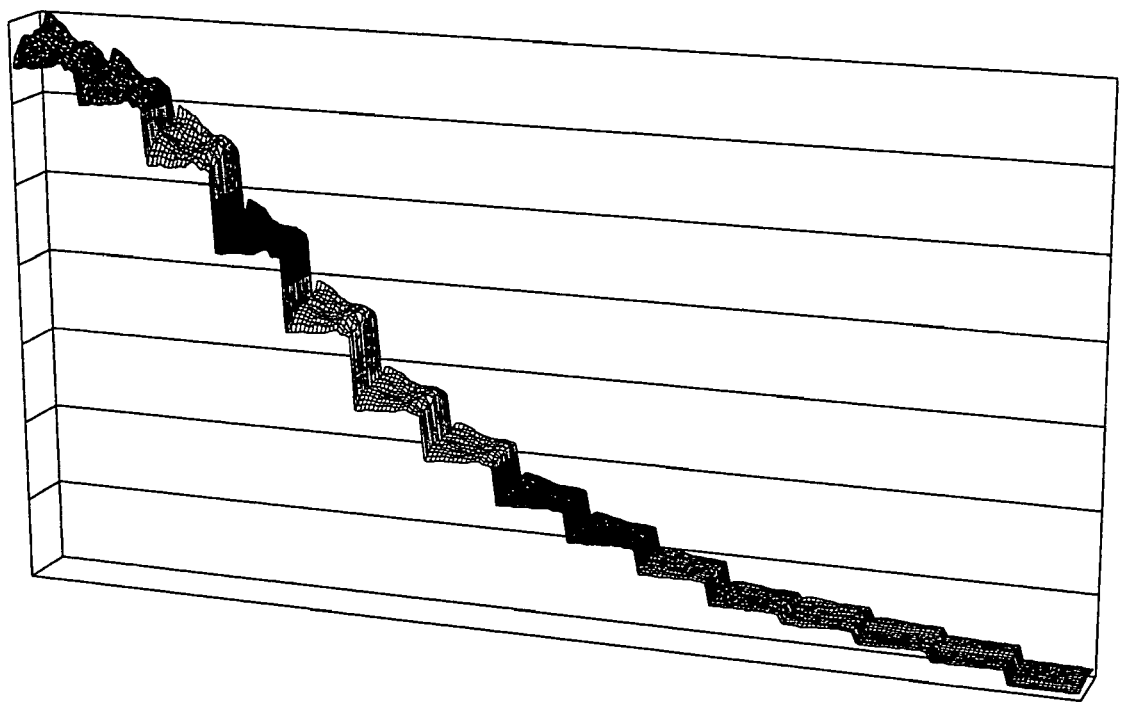
FIG. 19 is a drawing that shows the relationship between the output of the area sensor and the exposing time, obtained as the exposing time is reduced in a third embodiment

FIG. 19 shows the relationship between the output (axis of ordinates) of the area sensor 8a and the exposing time (axis of abscissas, with the exposing time being shorter toward the right side) when the exposing time is reduced. In this case also, since no light-irregularity correction is carried out within the area sensor 8a, the output between pixels is varied.

Figure 20:
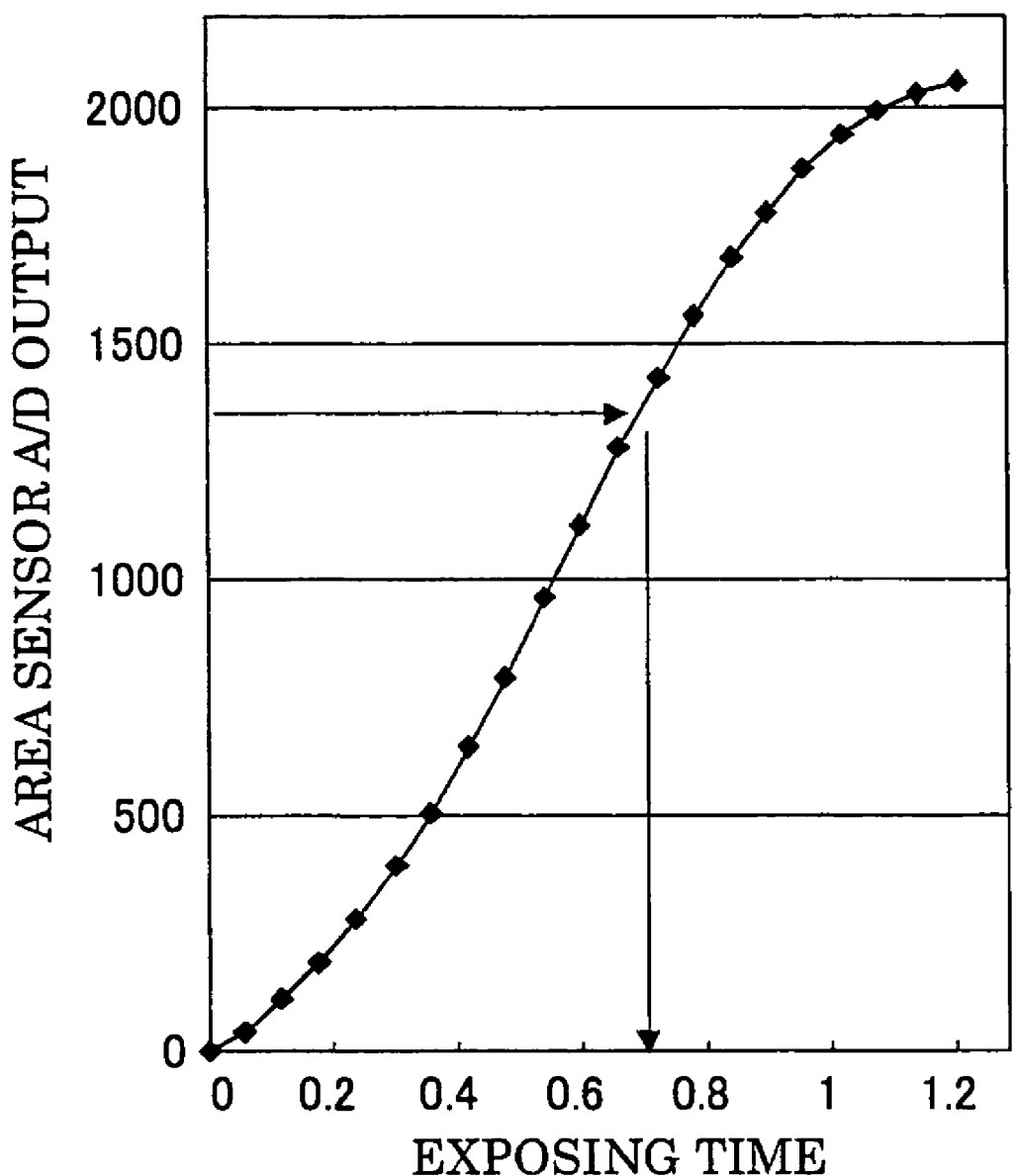
FIG. 20 is a drawing that shows the results of FIG. 19 with respect to one pixel of the area sensor.

FIG. 20 shows the relationship between the output and the exposing time with respect to each of the pixels, and the same results as those of FIG. 16 and FIG. 3 are obtained. The data shown in FIG. 20 is stored as linearizing data with respect to each of the pixels.

Figure 21:
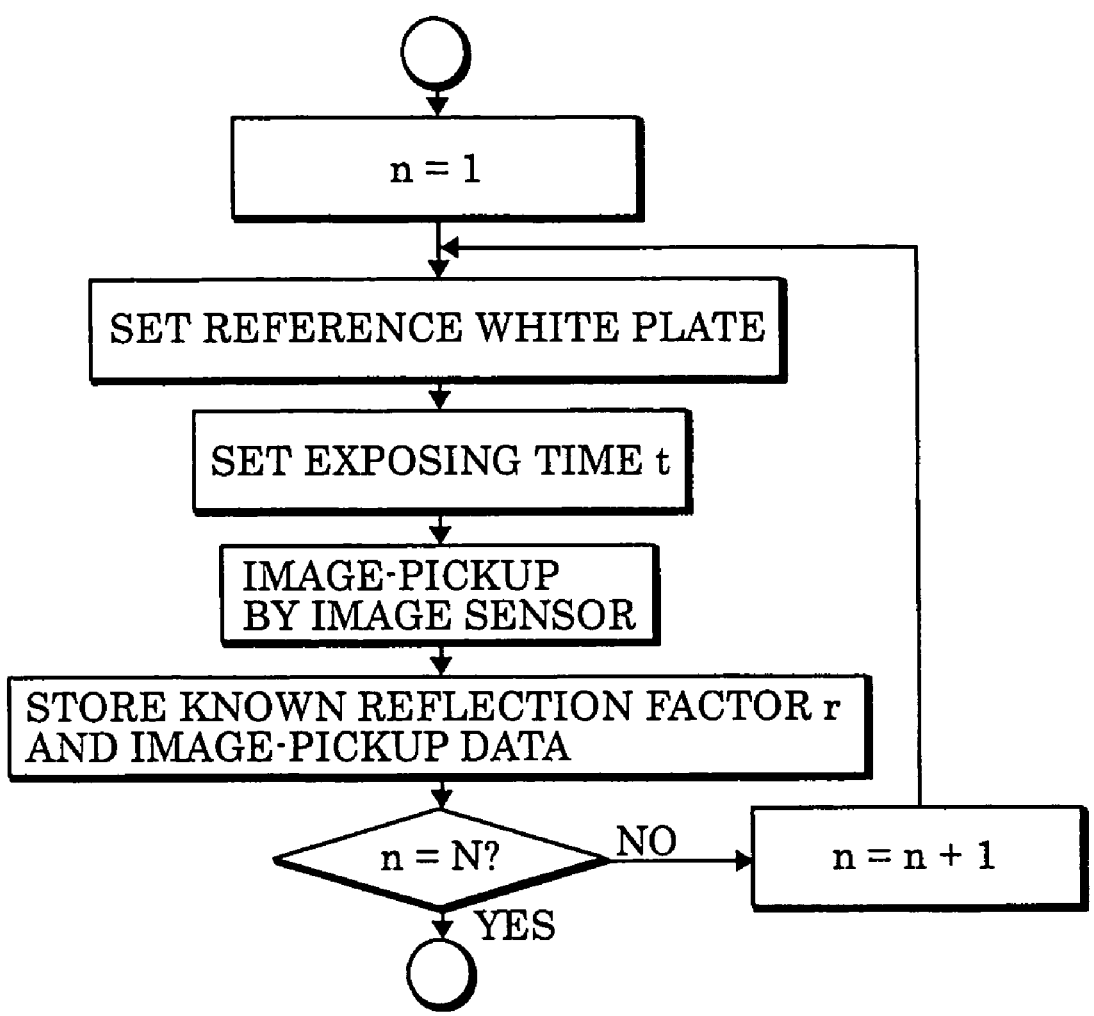
FIG. 21 is a flow chart that shows a sequence of processes carried out to obtain linearizing data in the third embodiment

FIG. 21 shows the sequence for acquiring the linearizing data in a collective manner. The reference white plate is set as the measuring object 2, with the reference exposing time t being set An image-pickup process is carried out by the area sensor 8a while light is applied during the corresponding exposing time so that the exposing time t and the image-pickup data are stored.

Next, the same measurements are repeated with the exposing time being reduced by 10%. In this manner, the measurements are repeatedly carried out with the exposing time being successively reduced; thus, the relationship between the sensor output and the exposing time with respect to each of the pixels is shown in FIG. 20. The exposing time on the axis of abscissas corresponds to the reflection factor.

Figure 22:
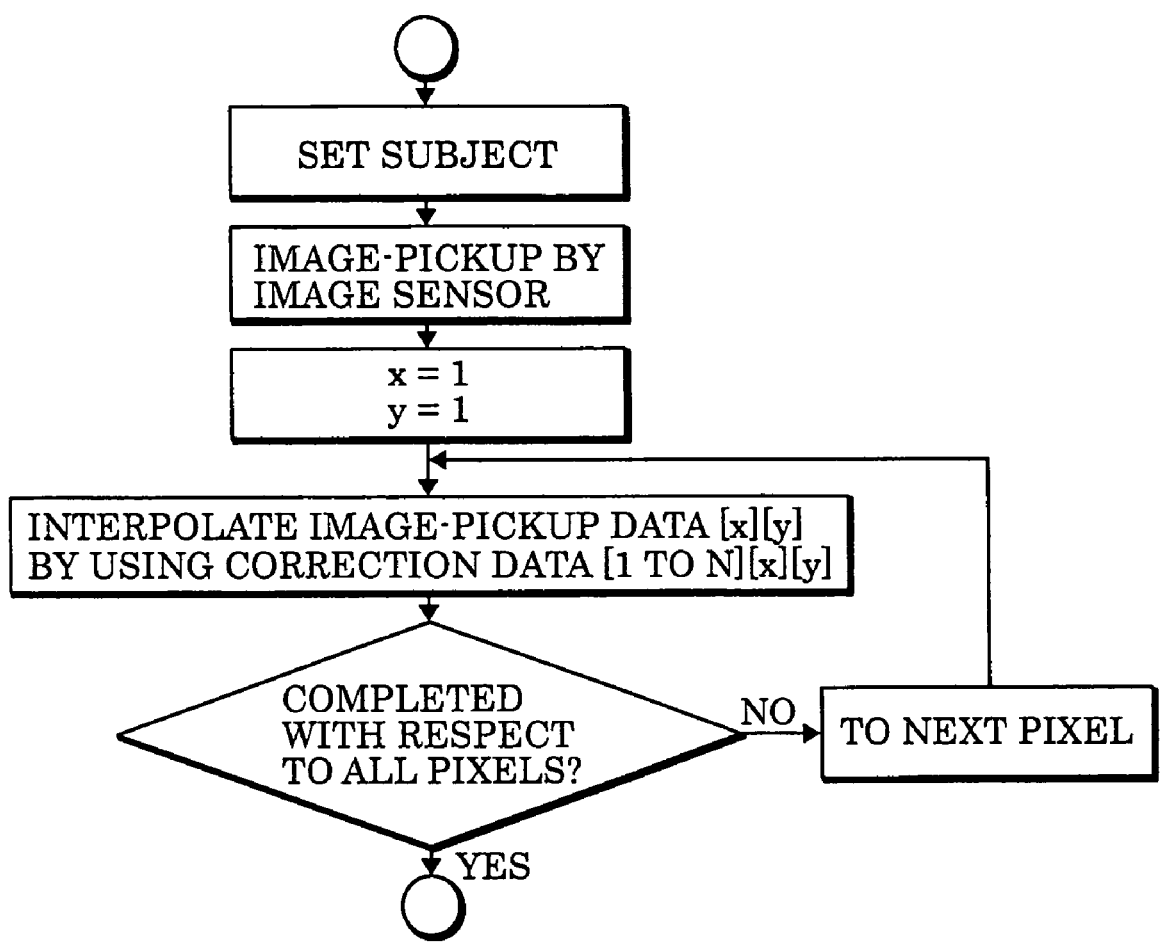
FIG. 22 is a flow chart that shows a sequence of reflection-factor measurements to be carried out on an unknown sample.

FIG. 22 shows a sequence of processes to be used for measuring a sample whose reflection factor is unknown, and this sequence is the same as that shown in FIG. 18. In this embodiment, the exposing time corresponding to the reflection factor is obtained with respect to each of the pixels.

Figure 23:
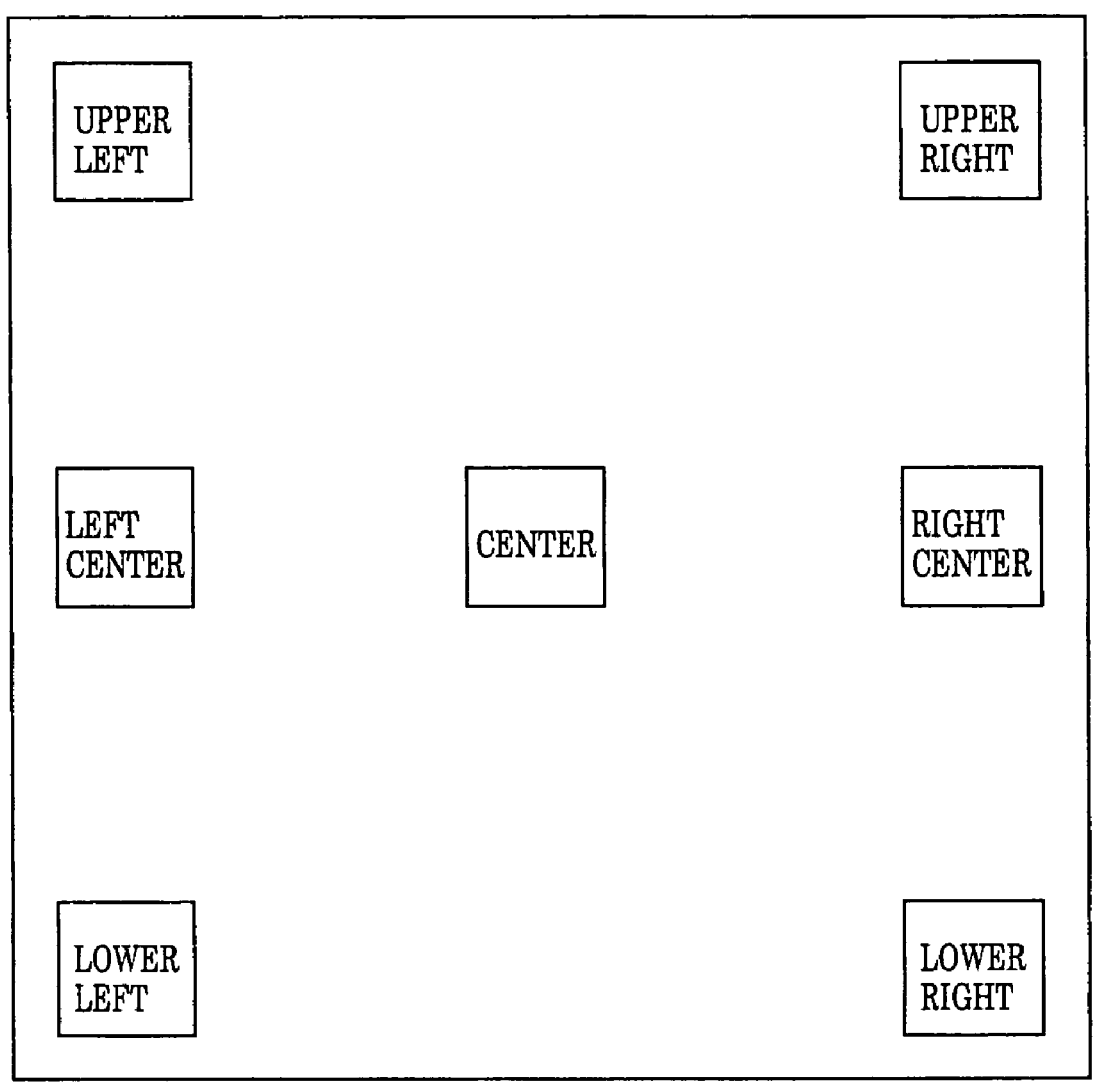
FIG. 23 is a plan view that shows data-acquiring pixel positions that are used for confirming data precision after correction in the third embodiment
Figure 24:
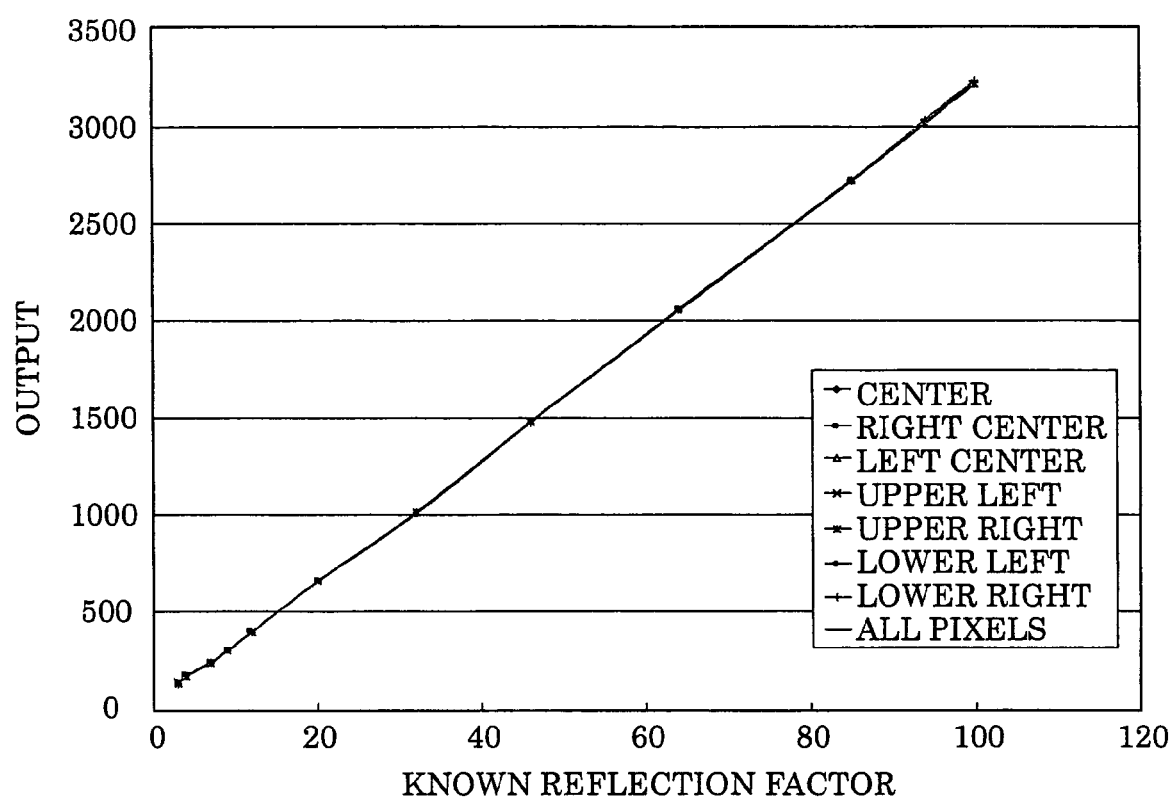
FIG. 24 is a graph that shows the relationship between the corrected output and reflection factor in respective pixels.

In this embodiment, data precision after the correction was confirmed. A plurality of image-pickup subjects, each having a known reflection factor, were measured. As shown in FIG. 23, pixels were selected at respective positions in the center portion and the peripheral portion of the area sensor 8a, and FIG. 24 shows the relationship between the corrected output and the reflection factor with respect to each of the pixels. The pixel output at each position may be an output from a single pixel or an average value of the outputs from some pixels in the vicinity of the position. The straight line represents the average value of all the pixels. In FIG. 24, the axis of abscissas represents the known reflection factor, and the axis of ordinates represents the corrected output.

The results shown in FIG. 24 indicate that irrespective of the pixel position within the area sensor 8a, it is possible to correct the non-linear property in the lens and the area sensor causing irradiation irregularities to a linear reflection factor-related value.

INDUSTRIAL APPLICABILITY

The correction method of the present invention is applied to various fields such as clinical inspection, food analyses and chemical analyses as a correction method for a sensor output in various analyzers including a dry chemistry analyzer in which a test sample bearing a reagent portion on its supporting member is used.

What is claimed is:

1. A correction method for a sensor output, which applies light to a measuring object and carries out measurements by receiving light reflected from a detection subject portion by a sensor, wherein
    said sensor lacking linearity in an output thereof in response to the quantity of received light, and
    said method comprises a linearizing process that corrects the sensor output so that the output from said sensor in response to a variation in the quantity of received light is made proportional to the quantity of received light, wherein said linearizing process comprises the following processes (A) and (B):
    (A) a process in which a photodetector having linearity in an output thereof in response to the quantity of received light is arranged so that light to be made incident on the sensor is simultaneously made incident on said photodetector, and upon variation in the quantity of incident light, a relationship between the sensor output and the output of said photodetector is stored as linearizing data; and
    (B) a process in which, upon measurement of a measuring object, the resulting sensor output is corrected and made proportional to the output of said photodetector based upon said linearizing data.

2. The correction method for a sensor output according to claim 1, wherein said sensor is an area sensor and said linearizing process is carried out on each of pixels.

3. The correction method for a sensor output according to claim 1, wherein said sensor is an area sensor, and said linearizing process is carried out by selecting some pixels in the vicinity of the brightest pixel within the image and using the average value of outputs of these pixels.

4. The correction method for a sensor output according to claim 1, wherein said sensor output corresponds to a value that is obtained after an offset process by subtracting an output at the time when the quantity of received light is zero as dark data from the output.

5. The correction method for a sensor output according to claim 1, wherein a photodiode is used as said photodetector whose output has linearity with respect to quantity of received light.

6. The correction method for a sensor output according to claim 2 or claim 3, wherein a CCD or CMOS sensor is used as said area sensor.

7. The correction method for a sensor output according to claim 2 or 3, further comprising a light-irregularity correction process which, after a reference object has been measured as a measuring object, corrects the outputs of the respective pixels so that corrected values, obtained by subjecting the corresponding outputs of the respective pixels of said area sensor to said linearizing process, are evenly adjusted.

8. The correction method for a sensor output according to claim 7, wherein a reference object is measured as a measuring object, and said light-irregularity correction process is carried out on image data by using a quantity of received light at a fixed ratio close to the saturated quantity of light with respect to the quantity of received light at the time when the pixel has reached a saturated quantity of light.

9. The correction method for a sensor output according to claim 7, wherein said reference object is a reflection plate having even in-plane density or a blank.

* * * * *